United States Patent
Elrod

(10) Patent No.: US 10,869,946 B2
(45) Date of Patent: Dec. 22, 2020

(54) SCENT CONTROL ACCORDING TO LOCAL CONDITIONS OF A SCENT CONTROL DEVICE

(71) Applicant: Scott A. Elrod, Lake Jackson, TX (US)

(72) Inventor: Scott A. Elrod, Lake Jackson, TX (US)

(*) Notice: Subject to any disclaimer, the term of this patent is extended or adjusted under 35 U.S.C. 154(b) by 5 days.

(21) Appl. No.: 15/992,561

(22) Filed: May 30, 2018

(65) Prior Publication Data
US 2019/0365941 A1    Dec. 5, 2019

(51) Int. Cl.
*A61L 9/12* (2006.01)
*A01M 31/00* (2006.01)

(52) U.S. Cl.
CPC ........... *A61L 9/122* (2013.01); *A01M 31/008* (2013.01); *A61L 9/12* (2013.01); *A61L 2209/11* (2013.01)

(58) Field of Classification Search
CPC ........ A61L 9/122; A61L 9/12; A61L 2209/11; A01M 31/008
See application file for complete search history.

(56) References Cited

U.S. PATENT DOCUMENTS

| | | | |
|---|---|---|---|
| 5,578,280 A | 11/1996 | Kazi et al. | |
| 6,039,212 A * | 3/2000 | Singh ................... | B65D 83/262 222/30 |
| 8,170,405 B2 * | 5/2012 | Harris ................. | A01M 1/2033 392/386 |
| 9,357,760 B2 * | 6/2016 | Anderson ........... | A01M 1/2022 |
| 9,439,995 B2 * | 9/2016 | Conroy ................. | B05B 7/2416 |
| 2005/0183576 A1 * | 8/2005 | Taylor ....................... | B03C 3/32 96/16 |
| 2008/0159907 A1 | 7/2008 | Joshi et al. | |
| 2009/0010800 A1 | 1/2009 | Resch et al. | |
| 2014/0366809 A1 | 12/2014 | Huck et al. | |

(Continued)

FOREIGN PATENT DOCUMENTS

JP    3423164 B2    10/1996

OTHER PUBLICATIONS

HowStuffWorks (2017) (Year: 2017).*

(Continued)

*Primary Examiner* — Donald R Spamer
*Assistant Examiner* — Brendan A Hensel
(74) *Attorney, Agent, or Firm* — Dorsey & Whitney LLP

(57) ABSTRACT

Embodiments of the invention relate to devices, systems, and methods for selectively emitting scent control material responsive to local conditions of a scent control device. The local conditions may dictate the effectiveness of a given set of output parameters of a scent control device. The scent control device accepts as input, one or more conditional inputs carrying information about the local conditions around the scent control device, such as weather conditions, elevation, barometric pressure, or functional status of the scent control device. Operational programs corresponding to the conditional inputs may be automatically selected based on the combination of conditional inputs to cause the output parameters of the scent control device to match or take into account the local conditions. The scent control device then outputs scent control material such as ozone at a rate effective to control one or more scents to a level that is not perceivable by animals or humans.

26 Claims, 9 Drawing Sheets

(56) References Cited

U.S. PATENT DOCUMENTS

2016/0363339 A1* 12/2016 Blackley ................. A61L 9/032
2018/0250431 A1    9/2018 Eide et al.

OTHER PUBLICATIONS

RoseIndia (2015) (Year: 2015).*
Certified English Translation of JP3423164.
International Search Report and the Written Opinion of International Application No. PCT/US19/34340, dated Oct. 7, 2019 (12 pages).

* cited by examiner

SCENT CONTROL ACCORDING TO LOCAL CONDITIONS OF A SCENT CONTROL DEVICE

BACKGROUND

Animals have an acute sense of smell and are capable of recognizing a human scent or any other scent that is indicative of possible danger, such as scent carried by equipment, even at long distances. To avoid being detected, hunters, photographers, researchers, etc., typically attempt to position themselves downwind of an animal or will try to mask their scent with commercially available "natural" scents. The "natural" scent may include animal scents (e.g., animal urine) or vegetation scents (e.g., pine). However, such "natural" scents will not mask human scents. Rather, the animals smell both scents, though the human scent may be relatively overpowered by the "natural" scent.

Weather conditions may affect scent elimination techniques. For example, strong winds may disperse human scent over a wide area, potentially exposing human scent to more animals. Accordingly, those interested in scent control continue to seek improved scent control strategies.

SUMMARY

Embodiments of the invention relate to devices, systems, and methods for controlling scents using selective oxidant output corresponding to local conditions.

A scent control device according to at least some embodiments is disclosed. The scent control device includes a portable oxidant source. The scent control device includes a controller operably coupled to the portable oxidant source, the controller including one or more operational programs stored therein to control output of an oxidant from the portable oxidant source, each of the one or more operational programs including oxidant output parameters associated with a combination of one or more conditional inputs. The scent control device includes one or more selectors operably coupled to the controller for inputting the one or more conditional inputs into the controller.

A scent control system according to at least some embodiments is disclosed. The scent control system includes a portable scent control device. The scent control system includes an oxidant generator. The scent control system includes a controller operably coupled to the oxidant generator, the controller including one or more operational programs stored therein to control output of an oxidant from the portable scent control device, each of the one or more operational programs including oxidant output parameters associated with a combination of one or more conditional inputs. The scent control system includes one or more selectors operably coupled to the controller for inputting the one or more conditional inputs corresponding to local conditions of the portable scent control device into the controller. The scent control system includes a remote computing system operably coupled to the one or more selectors, the remote computing system including at least one database of conditional inputs and corresponding oxidant output operational programs.

A method of selectively emitting scent control material responsive to local conditions of a scent control device, according to at least some embodiments, is disclosed. The method includes inputting one or more conditional inputs into a system including a portable scent control device. The method includes automatically selecting an operational program responsive to receiving the one or more conditional inputs, wherein the operational program includes one or more selected oxidant output parameters corresponding to the one or more conditional inputs, and the one or more selected oxidant output parameters are effective to cause the portable scent control device to emit oxidant at a selected oxidant output rate. The method includes automatically adjusting one or more output parameters of the portable scent control device to the one or more selected oxidant output parameters. The method includes outputting the oxidant from the portable scent control device at the selected oxidant output rate.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the invention, wherein identical reference numerals refer to identical or similar elements or features in different views or embodiments shown in the drawings.

DETAILED DESCRIPTION

Figure 1:
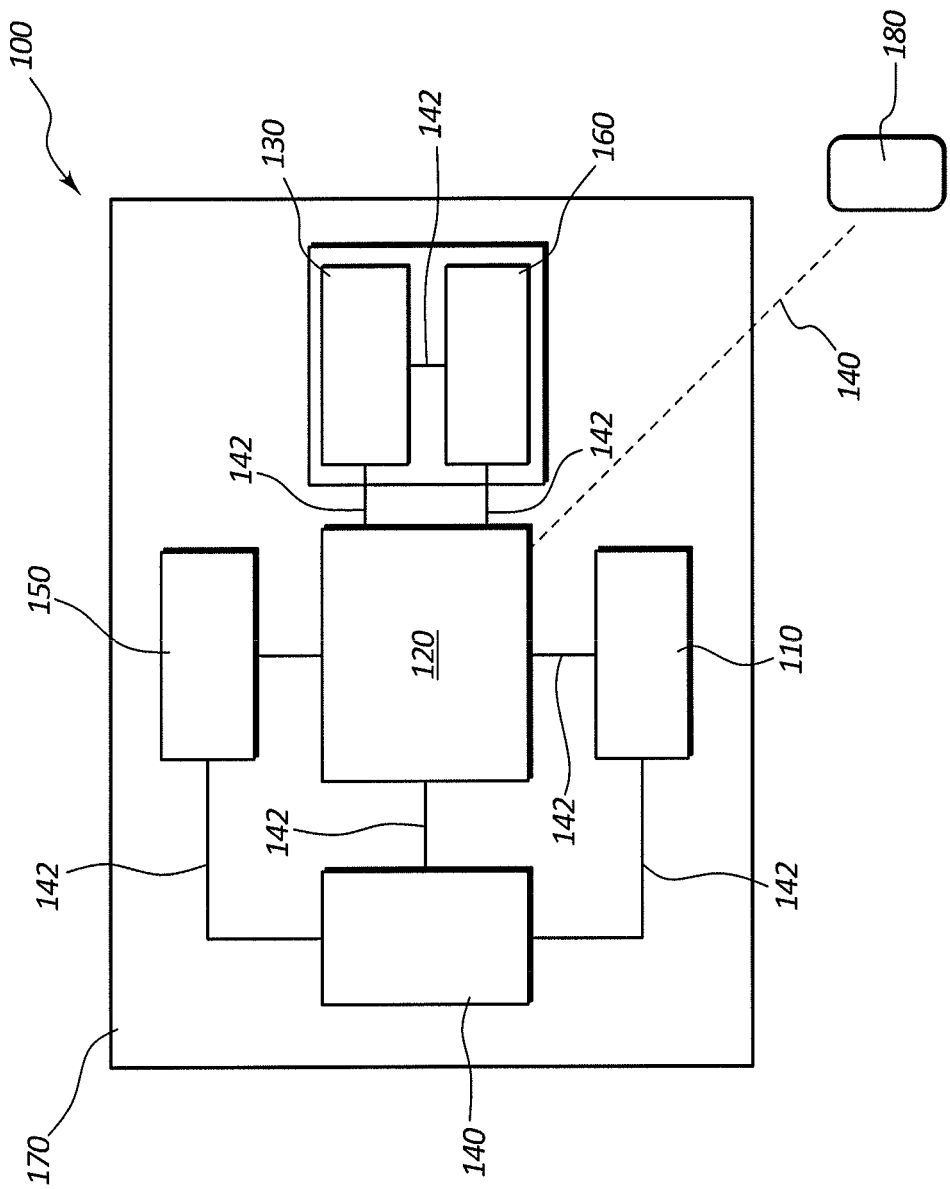
FIG. 1 is a schematic of a scent control device, according to at least some embodiments.

Embodiments of the invention relate to devices, systems, and methods for selectively controlling scent(s) responsive to one or more local conditions. The conditions may include environmental conditions, the functional condition of the scent control device, or even a condition of the user. In embodiments, a scent control device may be part of a system, or used in a method, for controlling or eliminating scent(s). Scent control, as disclosed herein, includes at least partially eliminating scent(s). Some scent molecules may be recognizable by animals or humans as being synonymous with humans or danger. Scent molecules are controlled or eliminated by the devices, systems, and methods herein by reacting the scent molecules with oxidants such as ozone to change the molecular structure of the scent molecules. Oxidation changes the molecular structure of the scent molecules to a new, different structure that is not readily recognized by animals or humans. For example, receptors in the olfactory system of an animal may be keyed to recognize a specific chemical structure, but when the specific chemical structure is altered via oxidation, the receptors may not recognize the altered chemical structure. Accordingly, the scent molecules may be effectively eliminated and replaced with unrecognizable derivatives or reactants. The derivatives may be detected, but are not associated with a humans or danger. Accordingly, scents are at least partially eliminated (e.g., controlled) by the devices, systems, and methods disclosed herein. By using the methods, devices, and systems disclosed herein, a user may alter the behavior of an animal, such as lowering an animal's perception of immediate danger by removing or otherwise obfuscating scents that animals associate with danger. The methods, devices, and systems disclosed herein also alter animal behavior by leading an animal to believe that a human is not present allowing the human to get closer to the animal than is otherwise possible.

While described in terms of scent control, the devices, systems, and methods disclosed herein may be used to oxidize any materials in an air volume or on objects, responsive to local conditions, not just to control scents.

The scent control devices disclosed herein include a portable oxidant source, a controller operably coupled to the portable oxidant source, and one or more selectors operably coupled to the controller for inputting, into the controller, one or more conditional inputs containing data of local conditions of the portable oxidant source. One or more conditional inputs may be input into the controller to provide data of the local conditions (e.g., physical conditions or location) to the controller. The one or more conditional inputs cause the controller to selectively control the output parameters of the portable oxidant source to direct the scent control device to effectively control scent(s) in various environmental (e.g., elevation, humidity, temperature, wind, etc.) and functional conditions. For example, the functional conditions of the portable oxidant source may account for different portable oxidant source models having different maximum outputs or a reduced function of a corona discharge plate in the portable oxidant source. Accordingly, a single scent control device, system, or method may be able to effectively control scents in any of a myriad of locations and conditions.

The inventors have discovered that an oxidant source running at a single output may be less effective in controlling scent(s) in some conditions (e.g., weather, elevation, etc.) to sufficiently prevent humans or animals from detecting the scent(s). However, the portable scent control devices, systems, and methods herein effectively control scents in any conditions, responsive to inputting conditional inputs into the device or system. Various devices and components for providing the conditional inputs and selectively adjusting oxidant output parameters are disclosed herein.

FIG. 1 is a schematic of a scent control device 100, according to at least some embodiments. The scent control device 100 includes a portable oxidant source 110, a controller 120 operably coupled to the portable oxidant source 110, and one or more selectors 130 operably coupled to the controller 120. The scent control device 100 may further include at least one fan 150 operably coupled to the controller 120, a power supply 140 operably coupled to one or more components of the device 100, a data connection 160 operably coupled to the controller 120 and the one or more selectors 130, and a remote control 180 operably coupled to the data connection 160. In practice, the one or more selectors 130 may be used to input one or more conditional inputs into the device (e.g., controller 120). The one or more conditional inputs may include at least one of weather conditions, location of the device, device functional conditions, or conditions of the user. The controller 120 includes one or more operational programs stored therein for controlling the output of oxidant from the device 100. The one or more operational programs include machine readable and executable instructions to control output of an oxidant from the portable oxidant source 110 according to oxidant output parameters corresponding to a combination of the one or more conditional inputs. Accordingly, the controller 120 selectively controls the output of oxidant from the portable oxidant source 110 responsive to the conditional inputs.

The scent control device 100 and the components therein may be sized and shaped to be carried by a single person in a single unit. For example, at least some of the components of the device 100 may be contained within or on a single housing 170. Each of the components of the device 100 is discussed in more detail below.

The portable oxidant source 110 provides one or more oxidants in gaseous form, vapor form, or droplet form. Gaseous oxidants may more readily disperse into an environment than vapor or droplet oxidants. The one or more oxidants may include one or more of ozone, diatomic oxygen, diatomic halogens, peroxides, radicals of any of the foregoing or components thereof, metastable oxygen, negatively charged metal oxides, encapsulated ozone, activated ozone, peracetic acid, chlorine dioxide, thixotropic gels, singlet oxygen, hypochlorite, or chlorite. Ozone and derivatives thereof (e.g., singlet oxygen, diatomic oxygen, atomic oxygen, metastable oxygen, or activated oxygen) may be particularly suitable for controlling scents (e.g., breaking down or reacting scent molecules or scent molecule sources). For example, ozone may be readily dispersed into an environment due to the relatively small size of ozone molecules relative to vapors or droplets of other oxidants such as most peroxides. Ozone is known to have an oxidation potential that is greater than nearly all oxidizers, with the exception of a small few such as fluorine or hydroxyl radicals. For example, ozone has be shown to react up to 10 times faster than chlorine. Additionally, ozone readily breaks down to harmless derivatives such as diatomic oxygen due to the inherent instability of the ozone molecule.

The portable oxidant source 110 may include an ozone generator such as corona discharge ozone generator (e.g., corona discharge plate), an ultraviolet ozone generator, an electrolytic ozone generator, or any other type of ozone generator. In some examples, the portable oxidant source includes an ionizer or electrostatic precipitator. The corona discharge ozone generator presents the advantages of being relatively small and efficient in comparison to other oxidant generators. The portable oxidant source may include a source of peroxides or derivatives thereof (e.g., hydroperoxides, hydroxyl radicals, or peroxide radicals). For example, a catalytic ionizer may provide oxidants. Catalytic ionization of air by ultraviolet light may produce a mixture of hydroxyl ions, hydroxyl radicals and hydrogen peroxide ions (as well as ozone). The oxidant generator may be an activated water or peroxide ion or radical generator, such as an electrolytic device for carrying out electrolysis of one or more of water or a peroxide. The portable oxidant source may include a fluid oxidant storage and a mist sprayer operably coupled thereto to spray a mist (e.g., droplets or micro droplets) of fluid oxidant.

The portable oxidant source 110 may be sized and shaped to be carried by a single person, such as in the device 100. For example, the portable oxidant source may include the oxidant generator, such as a corona discharge ozone generator, and the controller 120. In examples, suitable portable oxidant sources may include those found in the HR200, HR230, or HR400 ozone generators from Ozonics LLC, of Mason City, Iowa, U.S.A.

The portable oxidant source 110 may be controlled by the controller 120. The controller 120 may control each of the portable oxidant source 110, the one or more selectors 130, the power supply 140, the at least one fan 150, or the data connection 160 (e.g., communication port). The controller may be a part of, or separate from, the portable oxidant source 110. The controller 120 may be operably coupled to the portable oxidant source 110, the one or more selectors 130, the power supply 140, the at least one fan 150, or the data connection 160 via a hardwired or wireless connection. Suitable wireless connections may include any of Wi-Fi, Bluetooth, infrared, or radio frequency connections between components of the device 100. The hardwired connections 142 may carry one or more of power or data. Suitable hardwired connections 142 may include one or more of circuits, transistors, capacitors, resistors, electrical wiring, or any other tangible connection capable of carrying electrical bias(es) from one component to another.

The controller 120 is operably coupled to the portable oxidant source 110 to control generation or emission of oxidant, according to output parameters in one or more operational programs. The controller 120 includes one or more operational programs stored therein to control one or more output parameters of the portable oxidant source, such as amount of oxidant produced or emitted (e.g., per unit time), emission durations, or pulse durations. The machine readable and executable instructions control output of an oxidant from the portable oxidant source 110, such as via selective control of electrical bias supplied to the portable oxidant source 110. Each of the one or more operational programs include oxidant output parameters associated with a combination of one or more conditional inputs. For example, the operational programs include machine readable instructions to output oxidant at a higher rates via higher voltage parameters than instructions to output oxidant at a lower rate. The instructions to output oxidant at higher rates may be correlated to one or more conditional inputs, such as a combination of conditional inputs, by the controller 120. Accordingly, a combination of conditional inputs may prescribe a plurality (e.g., combination) of output parameters. Such output parameters include amount of electrical bias (e.g., voltage) delivered to the portable oxidant source 110 or duration of electrical bias delivered to the portable oxidant source. The output parameters may include pulsatile durations for pulsed emission of oxidant, pulse amplitude (e.g., amount of oxidant produced per unit time), durations for pulsed emission in addition to a normal operating amplitude, or pulse amplitude over a normal operating amount. The output parameters may include fan actuation, fan speed, or fan actuation duration for the fan 150. The output parameters may include a voltage delivered to the corona discharge plate (e.g., electrodes) for one or more standard or normal operation modes, such as an indoor or outdoor operation mode. The output parameter for the voltage delivered to the corona discharge plate may be at least 100 volts, such as 100 volts to 10,000 volts, 100 volts to 3,000 volts, 3,000 volts to 6,000 volts, 6,000 volts to 10,000 volts, less than 6,000 volts, less than 5,000 volts, at least 1,000 volts, at least 3,000 volts, or at least 4,000 volts.

The temporary boost mode voltage may include at least a 5% increase in voltage over the current operation mode, such as 5% to 80% more, 10% to 50% more, 20% to 40% more, or less than an 80% increase in voltage over the standard operation mode. The duration of the temporary boost mode (duration of the voltage increase over the standard indoor or outdoor mode) may be at least 30 seconds, such as 30 seconds to 2 hours, 1 minute to 1 hour, 5 minutes to 30 minutes, 10 minutes to 20 minutes, 5 minutes to 15 minutes, less than 1 hour, or less than 30 minutes. The current operation mode may be a standard indoor mode or standard outdoor mode.

The controller 120 may receive as conditional inputs one or more local conditions. The local conditions may include information about the conditions in the location of the device 100. The local conditions may include one or more of a wind speed, an elevation, a barometric pressure, a relative humidity, a temperature, or an indoor location of an area where the oxidant source is located. For example, each of the foregoing may affect the efficiency of the device or the effect of oxidant (e.g., ozone) on scent molecules in the local environment. In some examples, wind may disperse oxidant emitted from the portable oxidant source faster than a base emission rate allows for effective destruction (e.g., reaction) of scent molecules. In some examples, heat may cause oxygen molecules used to form oxidant and the oxidant to disperse and dissipate faster than in colder environments, or humidity may degrade or react with the oxidant to prevent the oxidant from reacting with scent molecules or sources of scent molecules. Relatively lower barometric pressure may lead to more oxidant dispersion in an environment than relatively higher barometric pressure. For example, it is currently believed that higher barometric pressure concentrates the oxygen available in the atmosphere relative to lower barometric pressure. Accordingly, it may be necessary to provide greater amounts of voltage to the corona discharge ozone generator to produce an effective amount of oxidant, when local conditions indicate lower barometric pressures. The reduces amount of oxygen for forming ozone may necessitate more voltage delivery to the corona discharge generator to produce the amount of oxidant to effectively oxidize scent molecules (or scent molecule sources such as bacteria) to at least a level where they are not detectable by a human or an animal.

The conditional inputs of local conditions may provide information to the controller 120 which may be used to select oxidant output parameters to effectively control scent molecules based at least upon the local conditions. For example, the controller 120 may have the oxidant output parameters stored therein as operational programs and automatically select the output parameters corresponding to any single or combination of local conditions, upon receiving the conditional inputs including the local conditions. In examples, normal (e.g., standard outdoor) operating mode of the oxidant source may be effective in winds up to 5 miles per hour (mph), but in winds of 50 to 10 miles per hour it may be necessary to increase the oxidant output by 10%-30% or 20% to 30%, while in 10 to 20 mile per hour winds it may be necessary to increase oxidant output by at least 20% such as 20% to 50% or 30% to 50%, in order to effectively control scent(s). In examples, windy conditions may also accompany relatively lower barometric pressures, which may require an additional increase in oxidant output parameters as discussed above.

In examples, the local conditions include an elevation, global positioning system (GPS) coordinates, or position with respect to wind obstructions (e.g., leeward side of a mountain). Higher elevations may lead to more oxidant dispersion (e.g., lower concentration of oxidant per unit volume of ambient air) than lower elevations, making it necessary to provide greater amounts of oxidant than at lower elevations to effectively oxidize scent molecules (or scent molecule sources such as bacteria) to a level where they are not detectable by a human or an animal. Similarly, the amount of ambient oxygen available to convert to ozone using a portable ozone generator is less than the amount at lower elevations. Accordingly, the scent control device 100 may include operational programs with output parameters that provide greater oxidant output (e.g., output parameters with higher outputs such as voltage) when conditional inputs indicate that one of the local conditions is a relatively higher elevation. The GPS coordinates may provide the location (e.g., position) necessary for the controller 120 to fetch data (e.g., elevation or weather) of local conditions corresponding to the location described by the GPS coordinates. The controller 120 may automatically incorporate any local conditions from the data and select oxidant output parameters corresponding thereto. The data may be regionally specific, with GPS coordinates of a geographic region being correlated to the local conditions and corresponding conditional outputs associated therewith, such as in a database.

In examples, local conditions include the model or type of portable oxidant source. Such examples may provide information as to the maximum output of the portable oxidant source. For example, some portable oxidant source models may have a relatively higher or lower base oxidant output level than other portable oxidant source models. In examples, local conditions include the functional status of the portable oxidant source. For example, the functional status may include the efficiency of a corona discharge ozone generator as a function of voltage input into the corona discharge plates. Accordingly, the controller 120 may select output parameters to account for a reduced efficiency of the portable oxidant source 110. For example, when the conditional inputs of the local conditions indicate that a corona discharge plate(s) is operating at a decreased efficiency (e.g., only 85% or less of the voltage delivered to the discharge plates is passed between the discharge plates to produce ozone), the controller 120 may automatically select oxidant output parameters corresponding thereto to compensate for the decreased efficiency. The local conditions may include the power supply status, such as the amount of charge in a battery, or a duration of operation based on the amount of charge in the battery.

In some examples, health data of a user or users may be part of the local conditions. For example, if a user sweats more or less than an average person, a conditional input for such a local condition may be used to provide more or less oxidant to ensure the scent from the sweat is controlled.

In examples, the output parameters of the one or more operational programs stored in the controller 120 are composed to direct a selected amount of oxidant output per unit time based upon the combination of the conditional inputs. For example, each conditional input may correspond to an amount of oxidant output per unit time. The controller 120 may add up the respective amounts of oxidant output per unit time corresponding to each conditional input (e.g., local condition) of the combination of conditional inputs to provide (e.g., run) an operational program that has oxidant output parameters that account for each conditional input (e.g., a sum of oxidant output parameters). In such a way, the scent control device 100 may selectively emit oxidant at varying levels based on the local conditions of the scent control device 100.

In examples, output parameters of the one or more operational programs stored in the controller 120 are composed to direct a selected amount of oxidant output per unit time based upon the value of the oxidant output parameters corresponding to the combination of the conditional inputs. For example, a base oxidant emission rate may be at least 50 mg of oxidant (e.g., ozone) per hour ("mg/hr"), such as 50 mg/hr to 1 g/hr, 100 mg/hr to 500 mg/hr, 500 mg/hr to 1 g/hr, 100 mg/hr to 200 mg/hr, 150 mg/hr to 250 mg/hr, 200 mg/hour to 400 mg/hour, 250 mg/hr to 350 mg/hr, 200 mg/hr to 300 mg/hr, 300 mg/hr to 400 mg/hr, 350 mg/hr to 450 mg/hr, 400 mg/hr to 500 mg/hr, 500 mg/hr to 600 mg/hr, 600 mg/hr to 700 mg/hr, 700 mg/hr to 800 mg/hr, less than 800 mg/hr, less than 500 mg/hr, or less than 300 mg/hr.

In examples, the output parameters of the one or more operational programs stored in the controller 120 are composed to direct a selected amount of oxidant output per unit time for a selected duration based upon the value of the combination of output parameters corresponding to the conditional inputs. For example, the output parameters may include an emission duration of one or more pulses of oxidant of at least a 5 second duration, such as 5 seconds to 12 hours, 30 seconds to 6 hours, 1 minute to 3 hours, 5 minutes to 1 hour, less than 6 hours, or less than one hour. The pulse durations may be at least 20 seconds, such as 20 seconds to 1 hour, 1 minute to 40 minutes, 2 minutes to 30 minutes, 3 minutes to 20 minutes, 5 minutes to 15 minutes, 5 minutes to 20 minutes, 20 minutes to 40 minutes, 40 minutes to an hour, less than an hour, less than 30 minutes, or less than 20 minutes. The pulses may be delivered according to a standard operating mode (e.g., relatively constant amount and duration of oxidant emission) or a temporary boost mode.

The temporary boost mode may include an increase in oxidant emission or generation over a base or current emission rate, such as at least a 5% increase, a 10% increase to a 30% increase, a 20% increase to a 40% increase, a 30% increase to a 50% increase, a 40% increase to a 60% increase, a 60% increase to an 80% increase, an 80% increase to a 100% increase, a 100% increase to a 200 increase, less than 150% increase, less than 100% increase, or less than a 50% increase in an amount of oxidant produced over the base or current emission rate. For example, a temporary boost mode operational program for temporarily increasing an amount of oxidant emitted from the portable oxidant source to a selected amount for a selected duration may include directions (e.g., operational instructions) to increase an output of the portable oxidant source by at least 30% for a duration of at least 1 minute. The base or current emission rate may be the standard indoor emission rate or the standard outdoor emission rate (e.g., greater emission amount than the indoor rate). The base or current emission rate may be a rate of oxidant emission that has been adjusted to account for local conditions as disclosed herein.

During the pulses of the temporary boost mode, an increased amount of oxidant (relative to a base or current emission rate) may be emitted into an environment for the selected duration to provide extra oxidant to control (e.g., destroy) scent molecules in the environment. During the pulses of the temporary boost mode, the increased amount of oxidant may be relative to an amount oxidant emission that was selected responsive to the conditional inputs. Accordingly, the oxidant output of the temporary boost mode may be relative to the output parameters selected responsive to local conditions. The temporary boost mode may be activated by the remote control 180, such as responsive to the behavior of an animal indicating that the animal is detecting a scent of the user, or responsive to a user determining that the level of oxidant output is insufficient to control an amount of scent in an environment (e.g., when a user is sweating).

In examples, the operational programs may include more than one standard mode, such as a standard indoor mode and standard outdoor mode. In such examples, the standard indoor mode may include a decrease in output parameters over the standard outdoor mode, such as decreases of the same magnitude of the increases disclosed above for the temporary boost mode. For example, the standard indoor mode may include at least a 5% lower oxidant output than the standard outdoor mode, such as 5% to 20%, 20% to 40%, 5% to 10%, 5% to 15%, 10% to 20%, less than 20% or less than 30% less than the oxidant output of the standard outdoor mode. The standard indoor mode may include pulsatile operation as disclosed herein. Accordingly, a single scent control device may be pre-programmed with standard operational modes for both indoor environments (e.g., a hunting blind or a room in a building) and outdoor environments (e.g., the field).

In some examples, the operational programs may include operational programs which include output parameters that vary based upon a time of day. For example, an operational program may include output parameters which take into account lower temperatures in the morning and higher temperatures as the day progresses, varying the amount of oxidant emitted based upon the time of day and the associated local conditions.

The operational instructions or programs (e.g., computer program product) including the standard operational modes and temporary boost modes may be stored in a memory or storage device within the controller 120. The operational programs may be accessed and executed by a processor within the controller 120. Embodiments of controllers are described in more detail below.

The one or more selectors 130 are operably coupled to the controller 120 for inputting one or more conditional inputs of local conditions of the portable oxidant source into the controller 120. In examples, the one or more selectors 130 include a plurality of direct inputs coupled to the portable oxidant source. The direct inputs may be selector dials, toggles, levers, digital inputs, or any other means of inputting a value for a conditional input into the device 100 (e.g., the controller 120). Each of the plurality of direct inputs may correspond to one of the one or more conditional inputs such as a wind speed conditional input, an elevation conditional input, a barometric pressure conditional input, a relative humidity conditional input, a temperature conditional input, or an indoor conditional input, etc. For example, the one or more selectors 130 may include a direct input (e.g., dial) for each of the conditional inputs (e.g., local conditions). In such examples, the scent control device 100 may include a dial for each local condition, such as wind speed, elevation, barometric pressure, relative humidity, temperature, or an indoor or outdoor conditional input.

In examples, the one or more selectors 130 may include a digital interface (e.g., a touch screen, a digital readout, one or more buttons, etc.) for inputting the local conditions as conditional inputs. For example, each conditional input may have a dedicated digital interface. In examples, a single digital interface may accept each of the conditional inputs, such as via programming which allows a user to toggle through the conditional inputs to change the values thereof. For example, a user may toggle through weather data or location data inputs to provide conditional input values to one or more of the weather or location data inputs.

Each of the direct inputs may be located on the housing 170 such that a user may access the direct inputs. Accordingly, the selectors 130 may be located on the scent control device to directly accept conditional input.

In examples, the one or more selectors 130 may include a data connection 160 for a network device coupled to the portable oxidant source 110, such as via the controller 120. For example, the data connection 160 may include one or more of a wired connection, a Bluetooth port, an infrared port, a radio frequency port, or a Wi-Fi port, operably coupled to the controller 120. The data connection 160 may be operably coupled to the controller 120 via a hardwired connection or another wireless connection (e.g., Bluetooth) to transmit conditional inputs or other inputs to the controller 120. In examples, the network connection may include a hardwired connection, such as a Universal Serial Bus (USB) port, Firewire port, etc.

The one or more selectors 130 may include the data connection 160 for a network device (e.g., smartphone, tablet, GPS receiver, a watch, a remote computing device, etc.) coupled to the portable oxidant source (via the controller 120). In such examples, the network device has access to location data for an area in which the scent control device 100 (e.g., portable oxidant source 110) is located. For example, the network device may include a smart phone or satellite phone connected to a server or computer with conditional inputs corresponding to the location of the network device or portable oxidant generator. The location data may include GPS coordinates of the area in which the portable oxidant source or network device is disposed. The location data may include one or more conditional inputs of the local conditions corresponding to the GPS coordinates. For example, the location data may include one or more of a wind speed conditional input, an elevation conditional inputs, a barometric pressure conditional input, a relative humidity conditional input, a temperature conditional input, or an indoor conditional input, or any other conditional input corresponding to the GPS coordinates. Accordingly, the scent control device 100 may automatically access and provide conditional inputs corresponding to GPS coordinates of the device 100 to cause the portable oxidant source 110 to selectively deliver oxidants at amounts that are effective to control scents under the local conditions described by the conditional inputs. In examples, the one or more selectors 130 are implemented as hardware (e.g., dials, toggles, etc.), software (e.g., operational instructions or portions thereof which accept values of conditional inputs), or firmware.

The power supply 140 may be operably coupled to the portable oxidant source, the controller 120, and the at least one fan 150, or any other components of the scent control device 100. For example, the power supply 140 may include one or more batteries (e.g. lithium-ion, nickel-cadmium, nickel-metal hydride, etc.) or portable chargers (e.g., power banks). The one or more batteries may be rechargeable. In examples, the one or more batteries may be modular battery packs, which may be removed and replaced. In examples, the one or more batteries have a connection for charging, such as a connection for the portable charger. In some examples, the power supply 140 may include a solar cell or a connection for a solar cell.

The power supply 140 may be a replaceable and rechargeable battery, such as a 12 volt battery. The rechargeable battery may be a lithium ion battery, lithium-ion polymer, a nickel-cadmium battery, nickel-metal hydride, lead acid, etc., batteries. The power supply 140 may include a plurality of rechargeable batteries. The rechargeable battery may be at least a 1 volt battery, such as 1.5 volts to 3 volts, 3 volts to 6 volts, 6 volts to 9 volts, 9 volts to 12 volts, 12 volts to 15 volts, 15 volts to 24 volts, greater than 12 volts, less than 24 volts, or less than 15 volts.

The controller 120 may be operably coupled to the power supply 140 or each component of the device 100, to selectively control the delivery of power to components of the device 100. For example, one or more operational programs may prescribe the amount and/or durations of power delivered to components of the device 100, such as the portable oxidant source 110, the controller 120, or the fan 150. Additionally, the power supply 140 may include a controller for controlling delivery of electrical biases therefrom.

In examples, the power supply 140 may include a cord or wired connection for connecting to a power outlet. For example, the power supply 140 may include 110 volt, 220 volt, or similar connections. The cord may allow the user to plug the scent control device 100 into a power outlet in a room, an extension cord, or a power station or power bank (e.g., battery pack or bank). Accordingly, the power supply 140 may include a wall outlet, the extension cord, or a power station or power bank. In examples, the power supply 140 may include both a wired connection for coupling to a power source and a battery pack. Accordingly, the scent control device 100 may be run with our without battery power. In examples, the wired connection may be provided as a detachable power cord which may be removed from the scent control device 100. The wired connection may serve to recharge the battery pack and provide power to the scent control device 100.

In examples, the at least one fan 150 is operably coupled to the controller 120 and positioned to propel oxidant produced in the portable oxidant source 110 away from the portable oxidant source 110. In examples, the scent control device 100 may include more than one fan, such as an intake fan, a cooling fan, an output fan, etc. Exemplary fans include microfans, centrifugal fans, cyclonic blowers, etc. Each fan 150 may be operably coupled to the power supply 140 and the controller 120, to activate, adjust speed, and deactivate according to operational instructions. For example, an output fan may be disposed adjacent to the portable oxidant source to propel the oxidant therefrom. In examples, an intake fan is positioned in the device 100 adjacent to the portable oxidant source 110 to draw air therethrough. Such an intake fan may provide an increase in oxidant output (e.g., ozone) by drawing elemental oxygen through electrodes (e.g., corona discharge plate) of the portable oxidant source when compared to a portable oxidant source without a fan. The intake or an output fan may purge oxidant or move ambient air through the portable scent control device 100. For example, ozone may remain on the corona discharge coils of a corona discharge ozone generator. In such examples, the ozone may degrade the coils if left in place. Ozone degradation may cause the ozone generator to lose efficiency and drain the battery of the scent control device. A short purge with ambient air may help void the coils of any ozone after production of ozone is halted. The intake or output fan(s) may remain in operation for at least at least 1 second after the portable oxidant source has ceased producing oxidant, such as 2 seconds to 2 minutes, 3 seconds to 10 seconds, 5 seconds to 15 seconds, 10 seconds to 20 seconds, 15 seconds to 30 seconds, 2 seconds to 30 seconds, 30 seconds to 1 minute, 1.5 minutes, 1.5 minutes to 2 minutes, less than 2 minutes, or less than 1 minute after the portable oxidant source has ceased producing oxidant. A cooling fan may be located in the device 100 to move air across the portable oxidant source 110, the controller 120, the power supply 140, or any other component of the scent control device 100 effective to cool the component. Any of the fans 150 may be used to move ambient air through the portable oxidant source 110 such as to flush oxidant from the local environment or allow the oxidant to dissipate as it reacts with substances in the local environment. Such flushing may be used in pulses to limit the concentration of oxidant in an environment such as an enclosed space (e.g., a container, a hunting blind, or a room).

In examples, the at least one fan 150 may be a variable speed fan that is controllable according to an operational program. For example, an operational program corresponding to a first set of conditional inputs may have a different (e.g., higher or lower) fan speed than a second operational program corresponding to a second set of conditional inputs.

One or more components of the scent control device 100 may be contained in housing 170. For example, each of the portable oxidant source, the controller, the power supply, the at least one fan, the data connection, or the one or more selectors may be disposed within or on the housing 170. The housing 170 may be made of a polymer (e.g., high density polyethylene, high density polystyrene, or polycarbonate), a composite (e.g., fiberglass or carbon fiber), a metal (e.g., steel, aluminum, alloys), a ceramic or cermet, any other material capable of withstanding impacts and preventing crushing of the contents of the housing 170, or combinations of any of the foregoing.

In examples, the housing 170 includes a one or more discontinuities defining air intakes, output ports (e.g., oxidant outlet port), or device ports (e.g., hole for selectors 130, hole for user interface, hole for electrical inputs, hole for battery port). For example, the housing may include a hole positioned and sized to accommodate a battery therein. In such examples, the power supply may include a replaceable battery pack and the hole (e.g. port) may accommodate removal and replacement of battery packs. In examples, the one or more discontinuities define a grill for an air intake or an output port.

In examples, the scent control device 100 includes the remote control 180 operably coupled thereto. The remote control 180 communicates to the data connection 160 and controller 120 via wireless signals 182. The remote control 180 is operably coupled to the controller 120 via the data connection 160 which may include a Bluetooth transceiver, an RF transceiver, or infrared transceiver to receive the wireless signals 182. In examples, the wireless signals 182 from the remote control 180 may initiate or terminate generation of oxidant, adjust an amount of oxidant output from the portable oxidant source 110, input the one or more conditional inputs, or initiate a temporary boost mode. For example, the remote control 180 may include one or more inputs, such as buttons, switches, or toggles, for activating the scent control device 100, deactivating the scent control device 100, selecting a mode of operation (e.g., standard indoor or outdoor), increasing or decreasing an output of the scent control device 100, entering one or more conditional inputs into the controller 120, initiating a temporary boost mode, or directing any other operation of the scent control device 100.

In some examples, the portable scent control device 100 includes a portable ozone generator and a controller that is operably coupled to one or more remote networks for communicating conditional inputs to the portable scent control device via a remote input device. The portable scent control device 100 may be automatically controlled (e.g., continuously, intermittently, or selectively) while a user is pursuing animals in the field (e.g., hunting) or prior to deployment. The scent control device 100 may be used in a system for automatically adjusting scent control delivery parameters according to local conditions of the scent control device 100. Such systems include remote computer network connections to provide conditional inputs corresponding to the local conditions.

Figure 2:
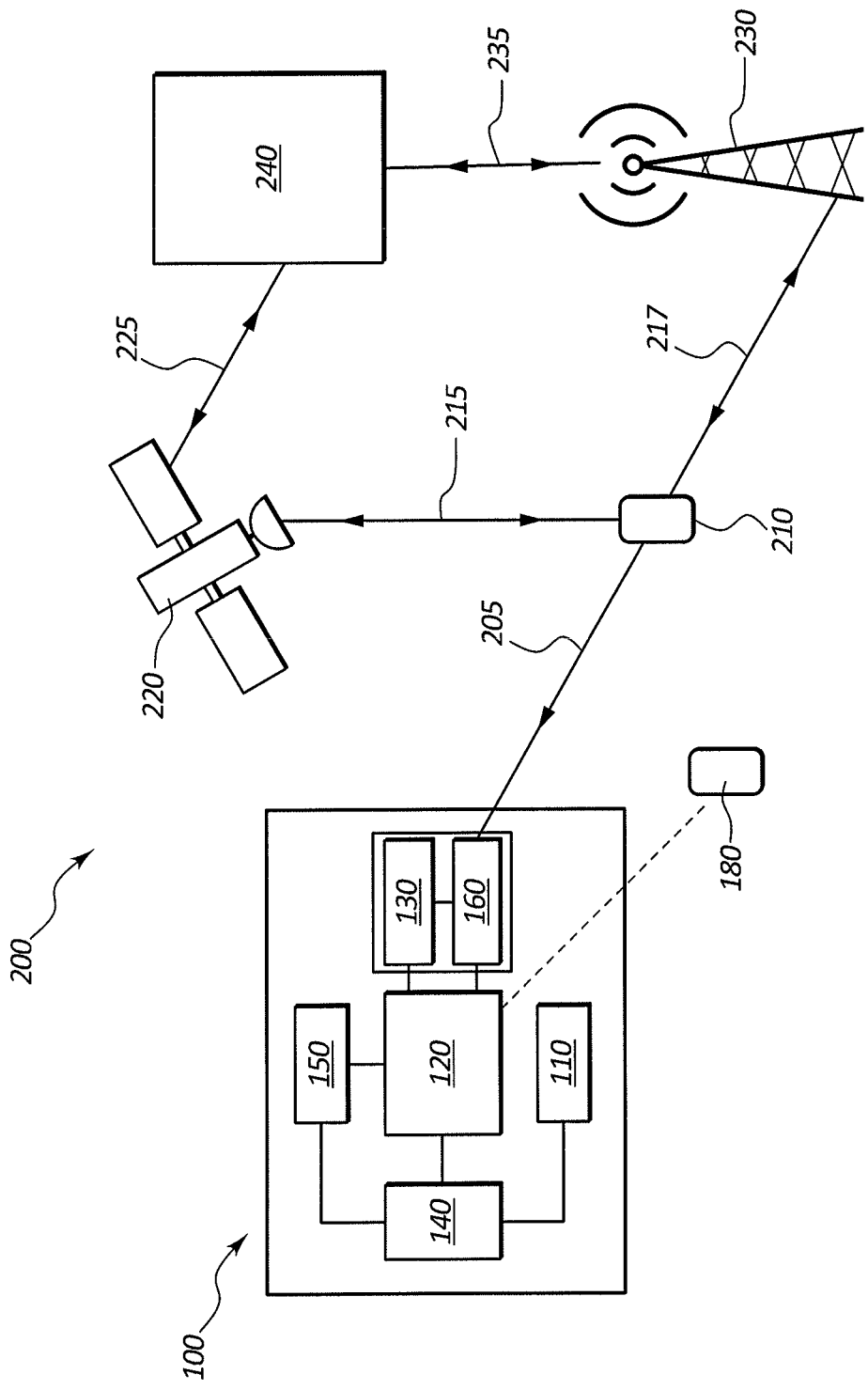
FIG. 2 is a schematic of a system for controlling scent, according to at least some embodiments.

FIG. 2 is a schematic of a system 200 for controlling scent, according to at least some embodiments. The system 200 includes the scent control device 100 and a remote computing system 240 operably coupled thereto. The remote computing system 240 is operably coupled to the scent control device 100 (e.g., the controller 120 thereof) via a remote input device 210. The remote input device 210 is operably coupled to the remote computing system 240 via one or more of a satellite network 220 or a cellular network 230. The remote input device 210 may receive conditional inputs such as GPS coordinates of the remote input device 210 or the scent control device 100 (or GPS coordinates of an intended use location) and communicate the conditional inputs to the remote computing system 240. The remote computing system 240 provides access to (e.g., connection to weather service Internet site or database) or a database of local conditions corresponding to the conditional inputs (e.g., GPS coordinates, elevation, etc.). The remote computing system 240 communicates one or more of conditional inputs (corresponding to the GPS coordinates, elevation, etc.) or an operational program corresponding to the conditional inputs (of the location of the GPS coordinates, elevation, etc.) to the remote input device 210, responsive to receiving the initial conditional input from the remote input device 210. The remote input device 210 communicates the conditional inputs to the controller 120 (e.g., via the one or more selectors 130) or the selected operational program to the controller 120 (e.g., via the data connection 160). Accordingly, the system 200 may automatically adjust the output parameters of the scent control device 100 to selectively provide an effective amount of oxidant to an environment to control scent(s) to undetectable levels at any location or under any local conditions.

As described above, the portable scent control device 100 includes the portable oxidant source 110 (e.g., oxidant generator), the controller 120, the one or more selectors 130, the power supply 140, the at least one fan 150, the data connection 160, the housing 170, and the remote control 180. In some examples, one or more of the above-noted components may be omitted from the scent control device 100. For example, the scent control device may not include the remote control 180. The controller 120 is operably coupled to the portable oxidant source 110 (e.g., oxidant generator) and the controller 120 includes one or more operational programs stored therein to control output of an oxidant (e.g., ozone) from the portable scent control device 100. Each of the one or more operational programs includes oxidant output parameters associated with a combination of one or more conditional inputs. As disclosed herein, the portable scent control device 100 includes one or more selectors 130 operably coupled to the controller 120 to receive one or more conditional inputs. For example, the one or more selectors operably are coupled to the controller 120 for inputting one or more conditional inputs corresponding to local conditions of the portable scent control device, into the controller 120. As noted above, the local conditions may include weather, elevation, model of portable oxidant source or scent control device, or functional condition of the portable scent control device (e.g., operational efficiency of one or more components of the scent control device, such as an oxidant generator).

The portable scent control device 100 includes the data connection 160 (e.g., Bluetooth, Radio Frequency, or infrared connection) for communicating with remote devices such as the remote control 180 or remote input device 210. In some examples, the one or more selectors 130 may include as a component thereof, the remote input device 210. That is, the remote input device 210 may be used to provide the conditional inputs to the controller 120, such as directly through a connection 205 to the data connection 160.

The remote input device 210 may include a cellular phone, a tablet, a computer (e.g., laptop computer), GPS receiver, mobile broadband modem, a watch, a proprietary remote control, or any other device with hardware and programming to communicate with a remote computing system 240, such as via a cellular network connection 217 (e.g., GSM, CDMA, LTE, AMPS, WiMAX, or any other wireless data network), satellite connection 215, Bluetooth, Wi-Fi, infrared, or any other wireless data connection. In examples, the remote input device 210 includes a cellular phone or watch, with global positioning system capabilities, operably coupled to the one or more selectors 130 and the cellular phone or watch is operably coupled to the remote computing system 240 via one or more of Wi-Fi, cellular network, Bluetooth, or satellite network connections.

In examples, the remote input device 210 is equipped to communicate with one or more of the satellite network 220 or a mobile device network (e.g., cellular network 230). For example, the remote input device 210 may be equipped to communicate with a plurality of satellites to determine the GPS coordinates of the remote input device 210. The remote input device 210 may include programming and hardware to determine the GPS coordinates of the remote input device 210, the scent control device 100, or a location of intended use of the scent control device 100, such as software for fetching GPS coordinates. For example, the remote input device 210 may include a mobile phone containing an application for determining or receiving the GPS coordinates of the mobile phone. In examples, the remote input device 210 includes a watch with global positioning system capabilities, operably coupled to the one or more selectors 130 and the remote computing system 240 via one or more of Wi-Fi, cellular network, Bluetooth, or satellite network connections. The watch may communicate with one or more global positioning satellites to obtain the current GPS coordinates of the remote input device 210 (watch), the user, and the scent control device 100. The watch may communicate with the global positioning satellites, one or more cellular networks, remote computing systems, the controller 120, the one or more selectors 130, and the data connection 160 as disclosed herein for any of the remote input devices 210. The remote input device 210 includes a wireless (e.g., cellular) network interface to communicate with a wireless network. The remote input device 210 may initiate or terminate generation of oxidant, adjust an amount of oxidant output from the portable scent control device, input the one or more conditional inputs, or initiate a temporary boost mode, by communicating data such as conditional inputs or operational programs between the remote computing system 240 and the controller 120. In examples, the remote input device 210 may be a remote control, such as the remote control 180 disclosed above. In such examples, the remote control 180 may include hardware and software adapted to allow the remote control 180 to perform the functions of the remote input device 210. In some examples, the system 200 may include both of the remote control 180 and the remote input device 210.

In some examples, the at least some of the functionalities of the remote input device 210 may be built directly into the scent control device 100 such as in the controller 120 and data connection 160. For example, the controller 120 may be programmed and equipped to communicate with the cellular network 230, the satellite network 220, and the remote computing device 240 such as via the connections disclosed below. In such examples, the scent control device 100 may directly communicate with the satellite or cellular networks (and the remote computing system). For example, the scent control device 100 may receive location information from global positioning satellites, communicate the same to the remote computing device, receive operational instructions or conditional inputs from the remote computing device, and automatically adjust the operational programs to selectively deliver oxidant, all without the separate remote input device 210. In such examples, the remote control 180 may be used to initiate and terminate operation of the scent control device 100 or the temporary boost mode, or select between standard indoor mode and standard outdoor mode.

In examples (not shown), the system 200 may include a plurality of scent control devices 100. In such examples, a single remote control 180 or remote input device 210 may control one or more operations of the plurality of scent control devices 100. In such examples, the single remote control 180 or remote input device 210 may be equipped and programmed to initiate and terminate operation of the scent control devices, automatically control the scent control devices, and initiate or terminate the temporary boost mode of the plurality of scent control devices 100. For example, the remote control 180 or remote input device 210 may have a selector to enable control of any combination of the plurality of scent control devices 100. For example, the remote input device 210 or remote control 180 may have a range selector or radiofrequency selector for sending instructions in a selected range or selected frequencies corresponding to one or more of the plurality of scent control devices 100. In examples, the plurality of scent control devices 100 may each communicate and receive conditional inputs or operational instructions from a single remote input device 210.

The remote computing system 240 is operably coupled to the cellular network 230 or the satellite network 220, such as through satellite connections 215 and 225. The remote computing system 240 includes one or more remote computing devices, such as servers, desktop computers, laptop computers, or groups thereof. The remote computing system 240 includes one or more computing systems, networks, or databases with access to current or forecast weather data, such as on the internet. In examples, the remote computing system 240 may include one or more computing devices (e.g., servers) which store local condition data for locations in the world. The one or more computing devices may fetch or continuously replace the local condition data from trusted sources such as the U.S. National Weather Service. The replacement or fetching may be periodic or on demand responsive to receiving conditional inputs (e.g., GPS coordinates) from the remote input device 210. One or more operational programs (e.g., software) stored in the remote computing system 240 may direct the replacement or fetching according to computer executable operational instructions therein.

The local condition data may be stored in the remote computing system 240 as conditional inputs. The remote computing system 240 may communicate each of the conditional inputs to the controller 120, such as via the remote input device 210 and the selectors 130, via the cellular network connections 217 and 235 or the satellite connections 215 and 225. In such examples, the controller 120 may receive the conditional inputs from the one or more selectors 130 or from the remote input device 210. The controller 120 may automatically select an operational program stored therein corresponding to the combination of the (current) conditional inputs to output the oxidant at output parameters providing a selected oxidant output rate corresponding to local conditions. As the selected rate corresponds to the combination of conditional inputs, the selected oxidant output rate is adapted to cause the portable oxidant source to output enough oxidant (e.g., ozone) to destroy or react enough scent molecules in the vicinity of the scent control device to render any otherwise recognizable scents unrecognizable to the sense of smell of an animal (e.g., deer or human). Accordingly, the scent control system 200 may selectively alter an output of oxidant to accommodate different local conditions, such as weather, elevations, or functional status of the scent control device.

In examples, the remote computing system 240 may receive the global positioning coordinates from a cellular phone, access a database of current conditional inputs available on the database for the location of the global positioning coordinates, and communicate the current conditional inputs to the cellular phone. The cellular phone (e.g., remote input device 210) communicates the current conditional inputs to the one or more selectors 130 and the controller 120. The controller 120 receives the current conditional inputs from the remote input device 210 or one or more selectors 130 and determines the corresponding operational program and initiates operation of the same. Accordingly, the communication of the conditional inputs from the remote computing system to the one or more selectors 130 is effective to initiate a selected operational program stored in the controller corresponding to the current conditional inputs to control production of the portable oxidant at a selected rate. In some examples, the communication of the conditional inputs from the remote computing system to the one or more selectors 130 is effective to select or load an operational program stored in the controller, and the portable scent control device may initiate said operational program upon actuation by the user (e.g., turning the device to active mode or initiating the operational program manually or via a remote device).

In some examples, the remote computing system 240 may receive as inputs, one or more of the GPS coordinates of the portable scent control device 100 or remote input device 210, a model of the portable scent control device 100 (e.g., or portable oxidant source 110 therein), or the functional status of the portable scent control device 100. The remote computing system may include operational programs stored therein. The remote computing system 240 may receive the conditional inputs and responsive thereto, automatically select an operational program corresponding to one or more of the conditional inputs or the local conditions corresponding thereto (e.g., local conditions of GPS coordinates or functional condition of the scent control device 100). For example, the remote computing system may access a database or source of current conditional inputs corresponding to the local conditions at the location of the GPS coordinates and correlate the same to a selected operational program stored therein that is composed to cause the portable scent control device to produce oxidant at a selected rate. The remote computing system 240 may communicate the selected operational program with the remote input device 210 via the cellular network connections 217 and 235, or satellite connections 215 and 225. The remote computing system 240 may communicate, with the remote input device 210, a program code identifying the corresponding operational program stored in the controller 120. In such examples, the transmission of data may be minimized which may be particularly useful where cellular network connections may be limited and prevent or hinder transfers of large amounts of data, such as operational programs. The remote input device 210 may communicate the operational program or program code identifying the operational program with the controller 120, such as via the remote connection 205 to data connection 160, effective to initiate production of the portable oxidant at the selected rate. The selected rate is effective to cause enough oxidant, such as ozone, to be emitted under current local conditions to at least partially dissociate scent molecules emanating from a user sufficient to prevent an animal in the location of the portable scent control device from detecting a scent of the user or the user's equipment.

The remote computing system 240 is operably coupled (e.g., indirectly) to the one or more selectors 130 such as via the cellular network 230 or the satellite network 220. For example, the remote computing system is operably coupled to the cellular network 230, which is operably coupled to the remote input device 210 which may form part of, or is operably coupled to, the one or more selectors 130 in communication with the controller 120. Accordingly, the remote computing system 240 is indirectly coupled to the controller 120 of the portable scent control device 100. Additional wireless connections between the remote input device 210 and the controller 120 may be included, such as RF, Wi-Fi, Bluetooth, or infrared connections (e.g., receivers, transmitters, or transceivers).

In examples, the output of the scent control device 100 may be continuously controlled or adjusted throughout a time period (e.g., day) via the remote input device 210 and the remote computing system 240 as disclosed herein. For example, the remote input device 210 may automatically and continuously (e.g., intermittently) communicate the location or local conditions around the scent control device 100 to the remote computing device 240 during the time period. The remote computing system 240 may automatically and continuously communicate current conditional inputs (or an operational program corresponding thereto) to the scent control device 100, such as via the remote input device 210. The remote input device 210 may continuously and automatically communicate the current conditional inputs (or an operational program corresponding thereto) to the scent control device 100 during the time period. The time period may be all of the time that the scent control device is active or may include only the time during which the portable scent control device is in an operational mode (e.g., while an operation mode is engaged). Accordingly, the system may self-regulate 200 production of oxidant according to local conditions of the scent control device 100 without continuous input from the user. In some examples, the system 200 may be operated only responsive to commands or requests issued by the user via the controller 120 or remote input device 210.

Figure 3:
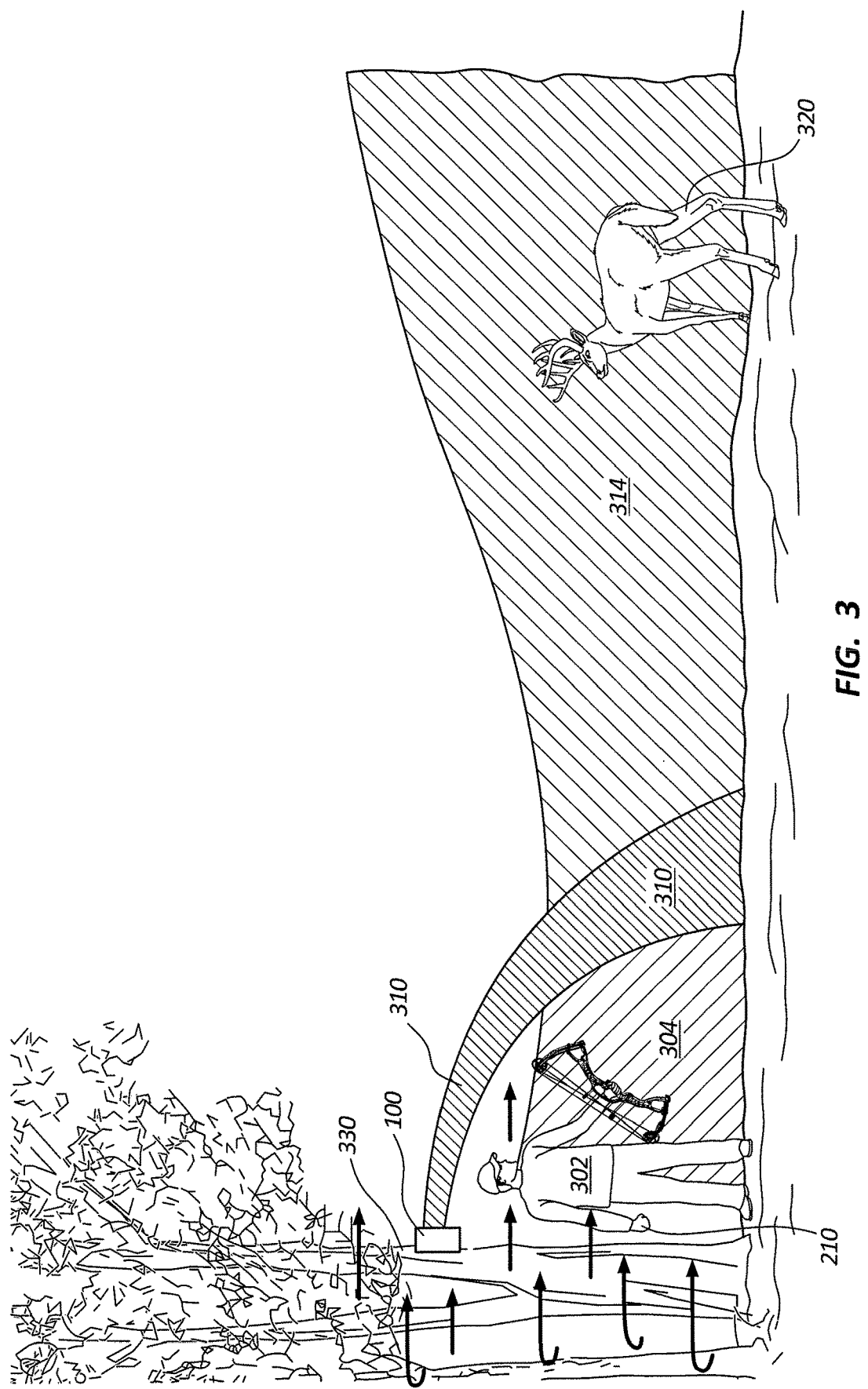
FIG. 3 is a schematic of the portable scent control device during use, according to some embodiments.

FIG. 3 is a schematic of the portable scent control device 100 during use, according to some embodiments. During use, the portable scent control device 100 may be used to cover, destroy, react, degrade, alter, or otherwise obfuscate one or more scents. For example, the portable scent control device 100 may be used to limit scents 304 synonymous with humans in the field, such as to hide the scents 304 of one or more of a person, their possessions, or their equipment from an animal 320. In examples, the one or more scents includes scents 304 that are synonymous with humans, such as body odors (e.g., thiol-containing excretions, carboxylic acid-containing excretions, sulfanylhexanol-containing excretions), breath odors (thiol-containing materials, sulfide-containing materials, etc.), perfumes, deodorants, colognes, equipment odors (e.g., detergents, fabric softeners, etc.), or derivatives (e.g., reaction or degradation products) of any of the foregoing. Animals 320 may include deer, elk, moose, antelope, goats, sheep, dogs, coyote, wolf, bear, cats, or any other animal. Although animals have different abilities to detect scents, the devices, systems, and methods therein allow a user to selectively hide their scent from any animal in any location or conditions. For example, the selectors and conditional inputs herein may include a selection for a type of animal pursued by a hunter, photographer, or researcher.

As the user 302 passes through or stays in a location, scents 304 (e.g., molecules) indicative of a human presence, possessions of a human, or equipment of a human emanate from the user 302. Some scent molecules (e.g., volatile organic compounds) have chemical structures that are recognizable (through the sense of smell) to animals as being synonymous with human presence. As these scent molecules are dispersed into the environment, such as by the wind or the user's movement through the environment, an animal may be able to detect said scent 304 via sense of smell even from long distances. For example, wind may carry the scent 304 downwind from the user 302 toward the animal 320.

As depicted, the portable scent control device 100 may be mounted near the user 302, such as in a tree 330. For example, the portable scent control device 100 may be mounted in the tree 330 that a user 302 is sitting near or sitting in. The portable scent control device 100 may be mounted in a tree stand or blind. In examples, the portable scent control device 100 may be mounted above the user 302, at or near head level of the user 302, behind the user 302, or even in front of the user 302. The scent control device 100 produces oxidant 310, such as ozone. The scent control device 100 produces the oxidant 310 in a curtain, cone, or cloud. As the scents 304 contact the oxidant 310, the oxidant 310 oxidizes the scent molecules in the scent 304. The portable scent control device 100 may be positioned to allow the scent 304 to pass through a curtain of oxidant 310 effective to hide the presence of the user 302 from the sense of smell of the animal 320. The oxidation changes the chemical structure of the scent molecules via reactions therewith to oxidized scent molecules providing an oxidized scent 314 (e.g., oxidized volatile organic compounds).

The oxidized scents 314 are not recognizable to animals as being synonymous with human presence. Field testing has shown animals do not become alarmed when detecting the oxidized scents 314. Additionally, animals do not become alarmed when detecting oxidants 310, such as ozone. Rather, these are foreign scents, that field testing shows, the animals do not associate with humans or any other alarming presence. Accordingly, the devices, systems, and methods herein may change the behavior of animals by changing (e.g., oxidizing) the scent molecules to an unrecognizable derivative allowing the animal to remain in a relaxed state when they normally would not if the scent molecules would not have been oxidized. Additionally, an animal that is showing visible signs that it is detecting a scent that it associates with danger may be calmed by outputting oxidant sufficient to eliminate or minimize (e.g., oxidize) the specific scent the animal is detecting. Such an output includes production of oxidant at a base rate or a flood of oxidant in a temporary boost mode as disclosed herein.

The portable scent control device 100 may be automatically adjusted to output enough oxidant to effectively hide the scents 304 from the animal 320 as disclosed herein, such as via conditional inputs to selectively control the amount of oxidant responsive to local conditions. The conditional inputs may be entered into one or more selectors on the scent control device 100 by the user, or automatically via a remote input device 210 (e.g., cellular phone) at the direction of the user 302.

In some examples, one or more scent control devices may be disposed around the user 302, such as behind (e.g., upwind) from the user 302, between the user 302 (e.g., downwind) and an animal 320, or behind an animal 320. In such examples, the multiple scent control devices may degrade, react with, mask, or otherwise eliminate scent molecules that animals or humans recognize as being scents that are synonymous with humans, over a wide area surrounding the user 302. Each of the one or more scent control devices 100 may be part of a single scent control system or may be an individual controlled scent control system. Each portable scent control device of a plurality of scent control devices may be operated in unison with each of the plurality of scent control devices (e.g., all according to a common operational program) or each may be controlled independently such as via the remote input device.

In some examples, one or more scent control devices may be carried by the user 302, such as in or on a pack carried by the user 302. In such examples, the pack (e.g., backpack) may be sized and shaped to allow the portable scent control device to output oxidant onto the user, such as onto a user's head, over a user's head, onto a user's torso, behind the user 302, or in front of the user 302. Such packs may include the Kinetic Pack (from Ozonics LLC of Mason City, Iowa, U.S.A.) or the like. In some examples, the scent control device may have one or more tubes extending from an oxidant output, wherein the outlets of the tubes are positionable to deliver oxidant to one or more areas of a user, such as the head, the armpits, the back, the torso, or any other area of a user. In some examples, the pack may include a sling or lanyard for wearing around the head or shoulders.

Figure 4:
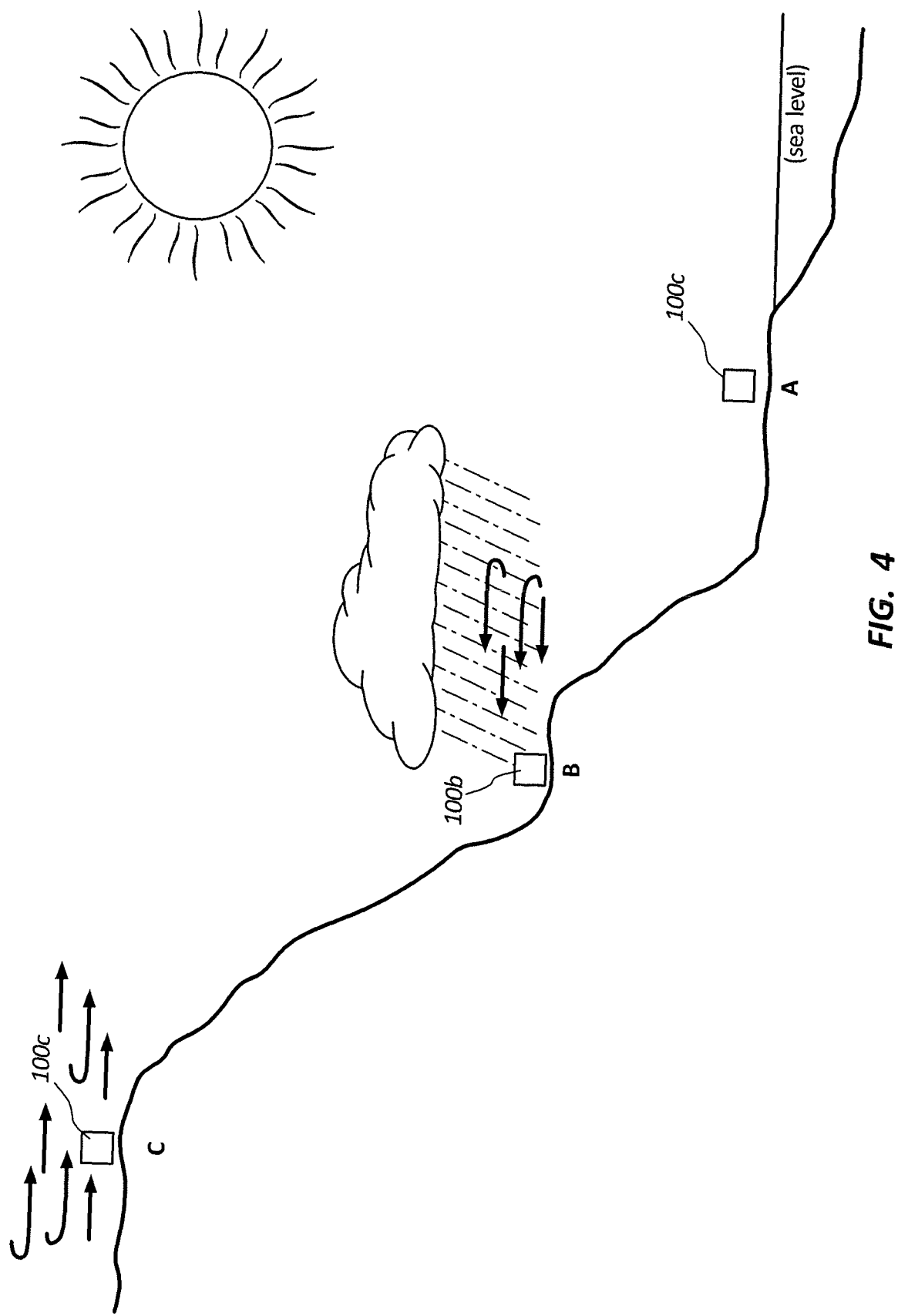
FIG. 4 is a schematic illustration of different locations having different local conditions, according to at least some embodiments.

FIG. 4 is a schematic illustration of different locations having different local conditions, according to at least some embodiments. FIG. 4 depicts the scent control devices 100a, 100b, and 100c, at different locations. The scent control devices 100a-100c or systems associated therewith may be similar or identical to any of the scent control devices or scent control systems disclosed herein, in one or more aspects. Each of the scent control devices 100a-100c may be identical to each other, with the only operational difference being the operational program automatically selected according to the combination of conditional inputs necessitated by the local conditions at each location. The locations A, B, and C each have unique local conditions. A single conventional scent control device operating at a single output level may not be able to provide oxidant output levels sufficient to control scents in the differing local conditions at locations A, B, and C. The scent control devices 100a-100c and systems associated therewith selectively control (e.g., adjust) the output parameters of the devices to output enough oxidant to effectively reduce, degrade, react with, or otherwise destroy one or more scents (e.g., scent molecules synonymous with a human or object).

For example, location A is at sea level, has a relative humidity synonymous with being adjacent to the ocean (e.g., high relative humidity), is not windy, and may be relatively hot compared to locations B and C. In such examples, the portable scent control device 100a or system associated therewith may output oxidant at a level commensurate with the local conditions at location A. For example, the conditional inputs for the above-noted local conditions may require less oxidant output due to a lack of wind, less oxidant output due to low elevation, more oxidant output due to high temperature, and more oxidant output due to relatively high humidity, all relative to a base oxidant output rate of the scent control device 100a.

Location B is at an intermediate elevation above sea level (e.g., 2000, 3000, 5000, etc., feet above sea level); has stormy weather with winds, precipitation, and the relatively humidity associated therewith (e.g., high relative humidity, above 50%); has barometric pressure associated with stormy weather (e.g., relatively low barometric pressure); and may be relatively colder than location A. In such examples, the portable scent control device 100b or system associated therewith may output oxidant at a level commensurate with the local conditions at location B. For example, the conditional inputs for the above-noted local conditions may require more oxidant output due to wind and precipitation, more oxidant output due to a relatively higher elevation, more oxidant output due to relatively low barometric pressure, and more oxidant output due to relatively high humidity, all relative to the base oxidant output rate of the scent control device 100b.

Location C is at a high elevation (e.g., at least 7000, 8000, 10,000, 12,000, etc., feet above sea level), has winds, has relatively low humidity (e.g., low relative humidity, below 20%), and may be relatively colder than locations A and B. In such examples, the portable scent control device 100c or system associated therewith may output oxidant at a level commensurate with the local conditions at location C. For example, the conditional inputs for the above-noted local conditions may require more oxidant output due to winds, more oxidant output due to a higher elevation, less oxidant output due to relatively low humidity, and less oxidant output due to relatively low temperatures, all relative to the base oxidant output rate of the scent control device 100c.

Further local conditions may be taken into account by the scent control devices or systems, such as model of the scent control device (e.g., maximum outputs), functional status of the scent control device, type of animal from which a scent is being hidden, etc.

In examples, the scent control devices 100a-100c may be the same device used in each of locations A, B, and C, but at different output parameters. In some examples, each of the scent control devices 100a-100c may be different devices (e.g., of the same model), used at different output parameters than the other devices 100a, 100b, or 100c. In any case, the portable scent control devices 100a-100c or scent control systems associated therewith may be used to automatically select and initiate production of oxidant at output parameters corresponding to the unique local conditions of the location of the scent control devices 100a-100c. The scent control devices 100a-100c may be operated as, and portions of, a scent control system, such as any of the scent control systems disclosed herein.

Figure 5:
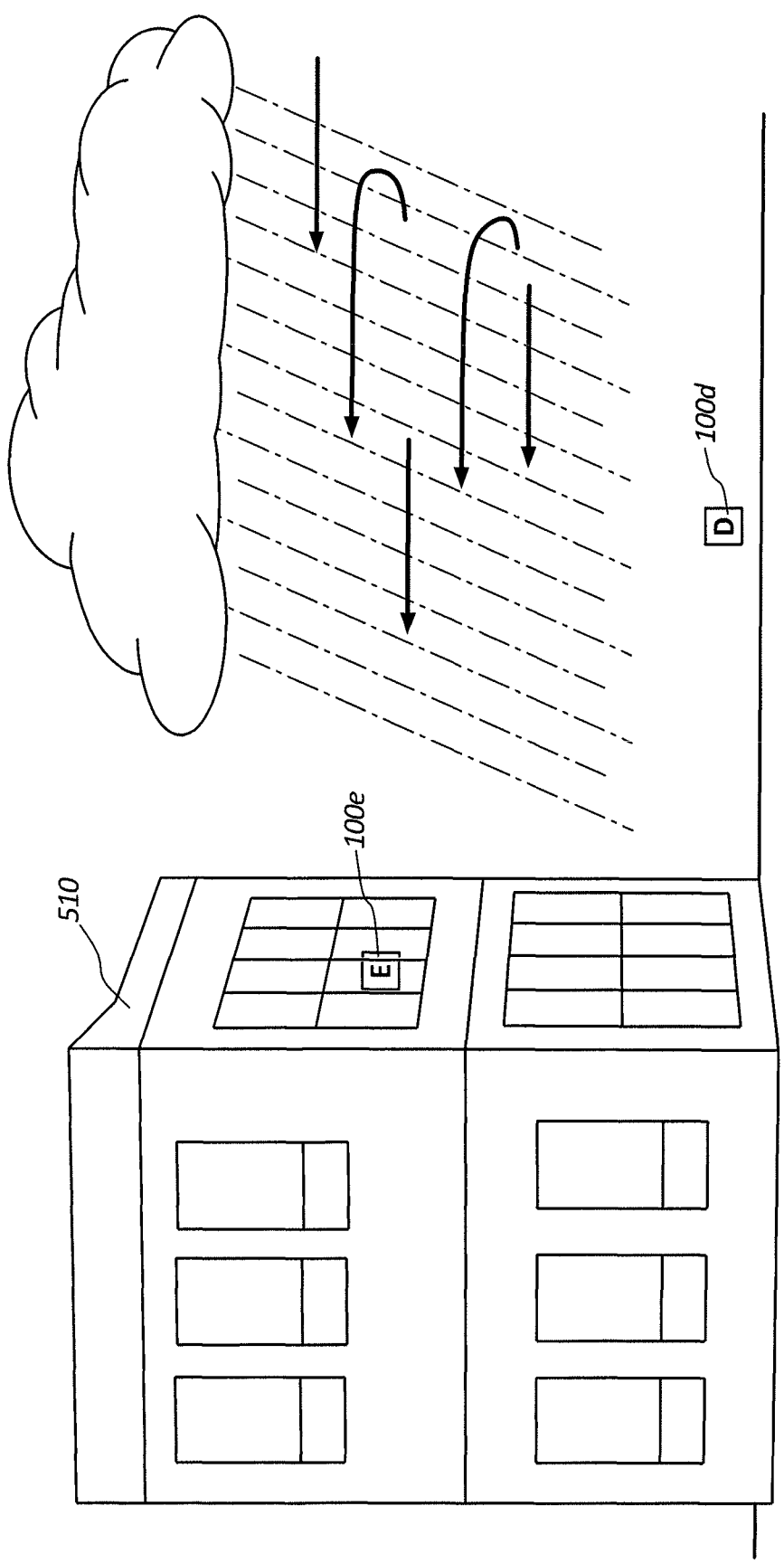
FIG. 5 is a schematic illustration of different environments at the same location each having different local conditions, according to at least some embodiments.

FIG. 5 is a schematic illustration of different environments at the same location each having different local conditions, according to at least some embodiments. FIG. 5 depicts the scent control devices 100d and 100e, in different environments at a single location. The scent control devices 100d or 100e or systems associated therewith may be similar or identical to any of the scent control devices or scent control systems disclosed herein, in one or more aspects. The environments at points D and E each have unique local conditions associated therewith. For example, the environment at point D is exposed to the elements which as shown may include weather, such as wind, temperature, humidity, and precipitation. The environment at point E may be an indoor environment inside of a building 510 which is controlled in one or more of humidity and temperature, and where wind is not a concern. In such examples, the scent control device may be used to control scents identifiable by humans or animals. For example, the scent control device 100*d* may control scents emitted from an exhaust or garbage collection area, while the scent control device 100*e* may control scents indoors, such as the smell of smoke from a cooking area, cigarettes, cigars, etc., the smell of a bathroom, pet smells in a living area, the smells emanating from a kitchen or garbage collection area, etc.

As noted with respect to locations A-C (FIG. 4), point D may be exposed to the elements. The scent control device 100*d* or system associated therewith may therefore automatically select (responsive to conditional inputs entered by the system or at the one or more selectors) an operational program that accounts for local conditions, such as weather, elevation, model of scent control device, or functional status of the scent control device as disclosed herein.

In indoor environments such as at point E in the building 510, the portable scent control device 100*e* and system associated therewith may be operated in an standard indoor mode. In examples, the standard indoor mode may be activated by a conditional input indicating that the local conditions include deployment indoors, an input on the device, or an input via the remote input device or remote control. The conditional inputs may also indicate a square footage or volume of the indoor area the scent control device is deployed in. Accordingly, the output parameters provided in the operational programs corresponding to indoor location of a certain volume may account for a volume of area to be treated with the oxidant. While at the same location as point D, the local conditions at point E may differ greatly from those at point D. The indoor mode may include an operational program that has output parameters that direct the portable oxidant source of scent control device to operate in a pulsatile manner, or a lower output, to ensure that levels of oxidant (e.g., ozone) do not exceed safe levels for human or animal exposure within the indoor environment while still providing effective control of scents to below perceptible levels. For example, the standard indoor mode may have lower oxidant output than the standard outdoor mode as explained herein. The standard indoor mode may include pulsatile operation where the oxidant is produced for a limited amount of time followed by flushing ambient air for a limited amount of time, each being repeated multiple times, as disclosed herein. By providing an amount of oxidant responsive to local conditions and in the pulsatile manner disclosed herein, the scent control devices, systems, and methods herein provide and maintain the concentration of the oxidant in the indoor space at a safe level while still providing effective scent control. Safe levels may be set in the operational program based on health guidelines (e.g., governmental recommendations). For example, safe ozone exposure levels may include up to 0.2 ppm for no more than 2 hours exposure, up to 0.1 ppm for 8 hours per day exposure with light exertion, up to 0.08 ppm for 8 hours per day exposure with moderate exertion, or 0.05 ppm for 8 hours per day exposure with heavy exertion. Accordingly, the scent control device 100*e* may safely control scents indoors responsive to receiving conditional inputs indicating that the scent control device 100*e* is indoors (e.g., via the one or more selectors).

The scent control devices 100*d* and 100*e* may be operated as, and portions of, a scent control system, such as any of the scent control systems disclosed herein.

In some examples, a microenvironment may be created to treat materials to remove scents therefrom. For example, a portable scent control device 100 may be operably coupled to an enclosure (e.g. space smaller than a room) to eliminate scents from objects and/or materials therein.

Figure 6:
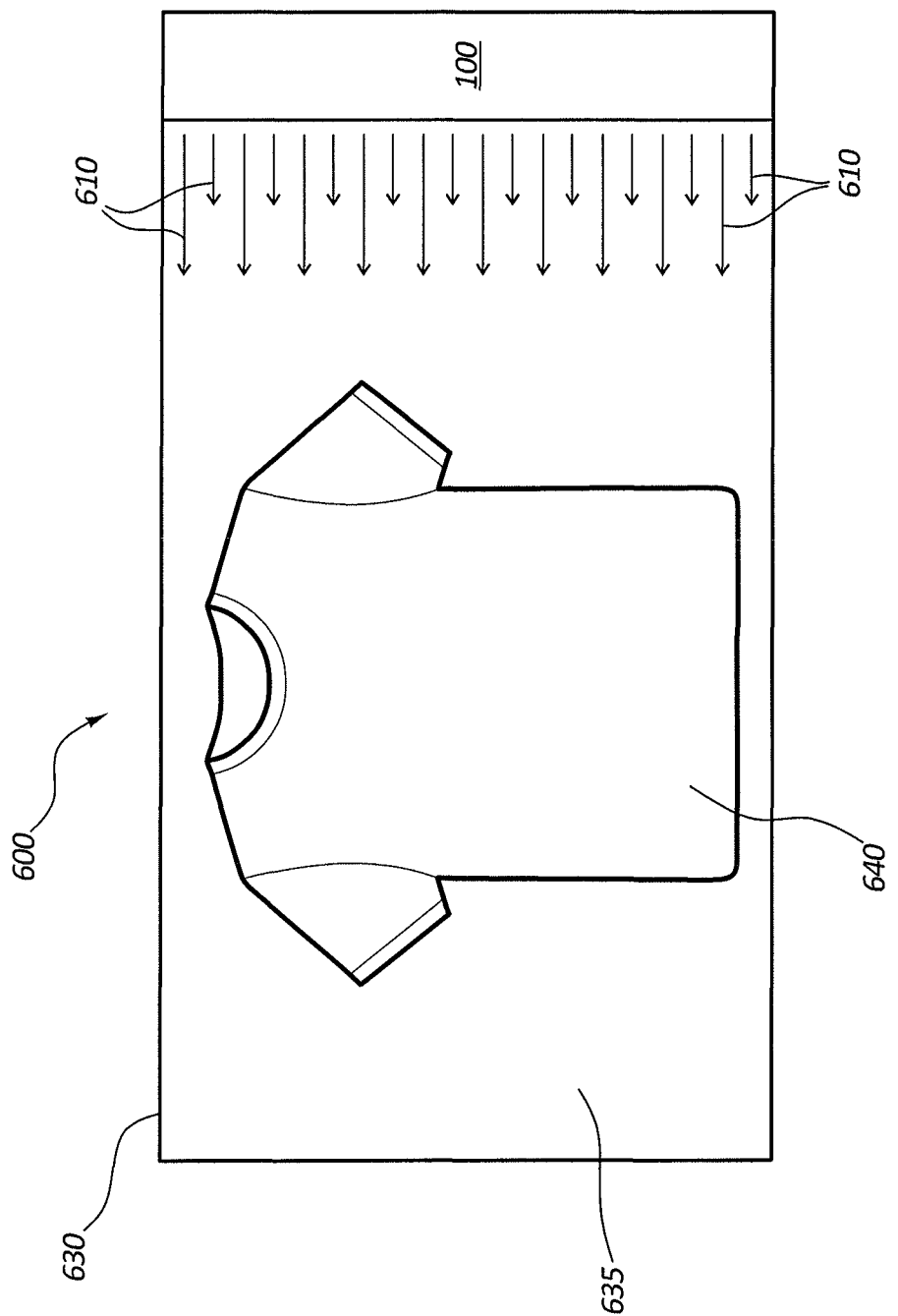
FIG. 6 is a block diagram of a system for controlling scents of objects, according to at least some embodiments.

FIG. 6 is a block diagram of a system 600 for controlling scents of objects, according to at least some embodiments. The system 600 includes the scent control device 100 and a container 630 fluidly coupled to the scent control device 100. One or more objects 640 held within the container 630 may be treated with oxidant(s) 610 from the scent control device 100 to remove any scents therefrom.

The portable scent control device 100 may be part of a scent control system 200, as disclosed herein. The portable scent control device 100 may be fluidly coupled to the container 630 via one or more conduits, ports, or other attachments. In some examples, the portable scent control device may be disposed within the container 630, or attached thereto at an oxidant port for receiving oxidant 610 from the scent control device 100.

The container 630 defines an interior region 635 for holding the one or more objects 640 therein. The container may be a bag, a box, a case, a cooler, or any other enclosure suitable to contain objects. In some examples, the container 630 may be substantially air tight, except for a connection to the scent control device 100. In some examples, the container 630 may be porous to allow some gases to escape from the interior region 635. The container 630 may include one or more ports to allow some gases to escape from the interior region 635.

In some examples, the container is made of one or more of a polymer, a fabric, a metal, wood, or oxidation resistant coatings on any of the foregoing. Suitable polymers may include any polymer, such as high or low density polyethylene, polyethylene terephthalate, polypropylene, polystyrene, or polyvinyl chloride. In some examples, suitable polymers include oxidant resistant polymers such as polysulfones, polyether ether ketone, polysiloxanes, etc. Suitable metals may include aluminum, tin, copper, zinc, iron, or alloys including combinations of any of the foregoing metals. Suitable fabrics may include natural fabrics such as cotton or wool, or may include synthetic fabrics such as polyester, a Nylon (e.g., polycaprolactam), polyurethane, or any other fabric made from synthetic materials. In some examples, the container 630 may include the DRI-WASH Descenting System from Ozonics LLC, of Mason City, Iowa, U.S.A, or bags that are similar thereto.

Conditional inputs include an indication that the oxidant is being input into a container, the volume of container, state of materials in the container (e.g., wet fabric), humidity, temperature, elevation, etc. The one or more operational programs that provide the output parameters for the scent control device include operational programs specifically tailored to treat objects, such as clothing, equipment, etc., with the oxidant at a level selected to eliminate scents to below the perceptible level of a human or animal, all within a defined volume in the container 630. It is known that oxidants may be degrade some materials, such as fabrics. The one or more operational programs may provide (e.g., direct the output of oxidant) levels of oxidant suitable to eliminate the scents yet still low enough to eliminate or at least limit degradation of the objects in the container 630 due to oxidation. For example, the operational programs for controlling or treating the scents of objects within the container may include operating the oxidant generator for a short time (e.g., at least 1 minute, 2 minutes to 5 minutes, 5 minutes to 10 minutes, etc.) to ensure that the objects, such as clothes in the container, do not degrade due to too much oxidation. In such examples, the on-time (e.g., amount of time that the oxidant is output from the portable oxidant source) may be followed by an off-time circulation of ambient air through the container 630. The off-time circulation may be accomplished by (the controller) executing operational instructions to direct the portable oxidant source to terminate operation while an intake fan runs or continues to run to circulate ambient air through the scent control device 100 into the interior region 635. The off-time circulation may be at least 1 minute, such as 1 minute to 10 minutes, 1 minute to 3 minutes, 3 minutes to 7 minutes, or 5 minutes to 10 minutes). In some examples, the operational program corresponding to the conditional input of eliminating scents in the container 630 may include multiple on-time and off-time cycles, in any combination of durations. For example, an operational program may include an on-time of at least one minute, followed by an off-time of at least one minute, followed by another on-time of at least one minute. Additional off-time and on-time cycles may be included in the operational program. In examples, the on-time and off-time durations or associated oxidant outputs may be supplemented or altered based on other local conditions provided to the controller as conditional inputs.

Objects 640 that may be treated to remove scent(s) therefrom include clothes, linens, towels, medical equipment and clothing (e.g., scrubs), hunting equipment, fishing equipment, packs, household items, or any other objects that from which a person wishes to remove scents and/or kill bacteria.

Figure 7:
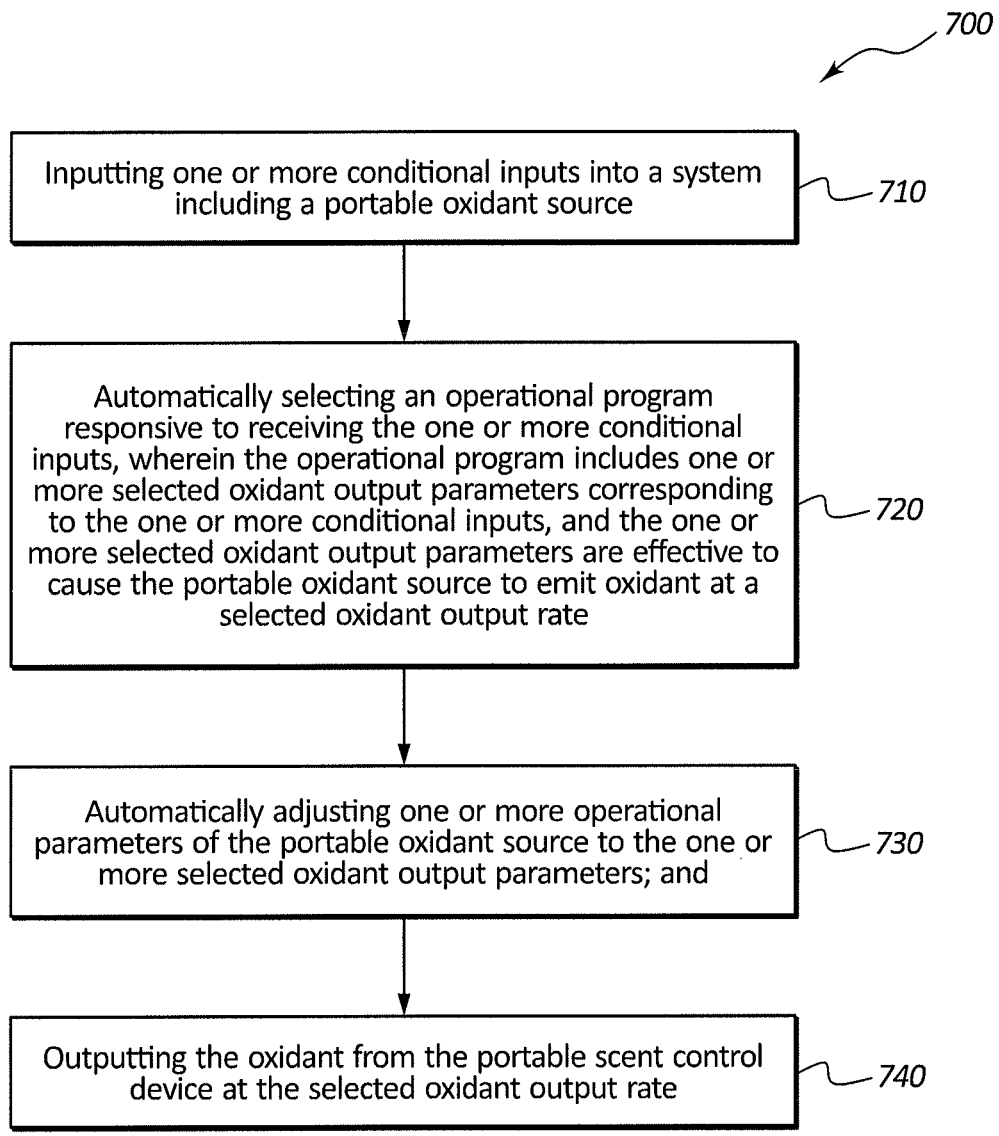
FIG. 7 is a flow diagram of a method of selectively emitting scent control material responsive to local conditions of a scent control device, according to at least some embodiments.

FIG. 7 is a flow diagram of a method 700 of selectively emitting scent control material responsive to local conditions of a scent control device, according to at least some embodiments. The method 700 includes the act 710 of inputting one or more conditional inputs into a system including a portable scent control device. The method 700 includes the act 720 of automatically selecting an operational program responsive to receiving the one or more conditional inputs, wherein the operational program includes one or more selected oxidant output parameters corresponding to the one or more conditional inputs, and the one or more selected oxidant output parameters are effective to cause the portable scent control device to emit oxidant at a selected oxidant output rate. The method 700 includes the act 730 of automatically adjusting one or more output parameters of the portable scent control device to the one or more selected oxidant output parameters. The method 700 includes the act 740 of outputting the oxidant from the portable scent control device at the selected oxidant output rate. Accordingly, the method 700 may selectively control, eliminate, or mask scents in an environment responsive to local conditions. The method 700 may include more or fewer acts than the acts 710-740. For example, the method 700 may not include the act 710.

The method 700 includes the act 710 of inputting one or more conditional inputs into a system including a portable scent control device. The system may be the system 200 (FIG. 2) disclosed herein, or any other scent control system disclosed herein. The portable scent control device may be the portable scent control device 100 (FIG. 1), or any other portable scent control device disclosed herein. In examples, the system or portable scent control device may include any components of any of the systems or scent control devices disclosed herein. For example, the system or portable scent control device may include the one or more selectors as disclosed herein. The one or more selectors may receive the conditional inputs from a user or remote input device.

Inputting one or more conditional inputs into a system including a portable scent control device may include manually inputting one or more conditional inputs into the selectors located on the portable scent control device. For example, inputting one or more conditional inputs into a system including a portable scent control device may include manually inputting one or more of a wind speed, an elevation, a barometric pressure, a relative humidity, a temperature, a functional status of the portable scent control device, or indoor location of an area where the portable scent control device is located, directly into a controller of the portable scent control device via a user interface thereon.

Inputting one or more conditional inputs into a system including a portable scent control device may include inputting one or more conditional inputs into the selectors of the portable scent control device via a remote input device (FIG. 2). Inputting one or more conditional inputs into a system including a portable scent control device may include transmitting the one or more conditional inputs into the portable scent control device via the remote input device over a wireless connection therebetween. The wireless connection may be a Bluetooth connection, a cellular connection, an infrared connection, a radio frequency connection, or any other wireless connection. Each of the conditional inputs may be transmitted to the controller of the portable scent control device via the one or more selectors and the data connection. In examples, the one or more selectors may be implemented as inputs for an operational program (e.g., software) composed to select an operational program for outputting oxidant corresponding to conditional inputs of local conditions.

The one or more conditional inputs may include one or more of any of the conditional inputs disclosed herein, in any combination. In examples, inputting one or more conditional inputs into a system including a portable scent control device may include inputting one or more of a wind speed, an elevation, a barometric pressure, a relative humidity, a temperature, a functional status of the portable scent control device, an animal that the scent is being controlled to deceive, or indoor location of an area where the portable scent control device is located, into the system. In examples, inputting one or more conditional inputs into a system including a portable scent control device includes inputting a global positioning location of the portable scent control device to a remote computing device of the system (e.g., of the remote computing system) via a remote input device such as one or more of a satellite phone, a cellular phone, a global positioning system receiver, or a remote control, operably coupled to the remote computing device. In examples, inputting one or more conditional inputs into a system including a portable scent control device includes inputting a location of the portable scent control device such as indoors or outdoors, a volume of an indoor environment, a location of the portable scent control device in or fluidly coupled to a container, volume of the container, or a type of object in the container.

The one or more selectors communicate the conditional inputs to the controller to cause the controller to automatically select the operational program corresponding to the local conditions described by the conditional inputs.

In examples, inputting one or more conditional inputs into a system including a portable scent control device may include transmitting GPS coordinates or any other local conditions (e.g., indoor or outdoor location) to a remote computing device. In such examples, the method 700 may also include receiving or determining the GPS coordinates (or other local conditions) of the remote input device or portable scent control device with the remote input device. The remote input device may transmit the GPS coordinates or other local conditions to the remote computing device via a satellite connection, cellular network connection, or any other data connection. The remote computing device may automatically correlate the local conditions such as GPS location to conditional inputs of the local conditions at the GPS location. The local conditions may include any of the local conditions disclosed herein such as one or more of weather conditions, elevation, etc. The remote computing system may communicate the conditional inputs or an operational program corresponding thereto back to the remote input device (e.g., cellular phone). The remote input device may communicate the conditional inputs or operational program with the controller as disclosed herein. Accordingly, inputting one or more conditional inputs into a system including a portable scent control device may include obtaining conditional inputs from a remote source based at least on a location of the portable scent control device and inputting those conditional inputs into the portable scent control device (e.g., via selectors provided as software or firmware).

In some examples, the one or more selectors may be located in a program located in the remote input device, wherein upon receiving the one or more conditional inputs from the remote computing device or from manual input (e.g., via a user entering values into fields on a user interface of the operational program), the remote input device automatically selects the operational program or communicates each conditional input with the controller via a data connection therebetween. For example, the one or more selectors may be implemented as part of a control program, wherein the one or more selectors are portions of the control program that accept the conditional inputs and communicate the same to another portion of the control program which automatically selects an operational program to output oxidant responsive to the conditional inputs. Examples of communication of data between the controller and the remote input device and the remote input device and the remote computing system are disclosed herein and may be utilized as portions of the method 700 for the purposes described herein, without limitation.

Inputting one or more conditional inputs into a system including a portable scent control device may include continuously, intermittently, or selectively inputting the one or more conditional inputs into the selectors of the portable scent control device.

The method 700 includes the act 720 of automatically selecting an operational program responsive to receiving the one or more conditional inputs, wherein the operational program includes one or more selected oxidant output parameters corresponding to the one or more conditional inputs, and the one or more selected oxidant output parameters are effective to cause the portable scent control device to emit oxidant at a selected oxidant output rate. In examples, automatically selecting an operational program responsive to receiving the one or more conditional inputs, may be carried out by the controller of the portable scent control device. The controller may include a program thereon which automatically correlates the conditional inputs with an operational program having output parameters corresponding to the local conditions described by the conditional inputs. In examples, automatically selecting an operational program responsive to receiving the one or more conditional inputs, may be carried out by a remote input device or even a remote computing device of a system containing the portable scent control device, as disclosed with respect to FIG. 2.

The operational program includes one or more selected oxidant output parameters corresponding to the one or more conditional inputs (e.g., the local conditions described by the conditional inputs). The selected oxidant output parameters may be absolute output parameters, that is, output parameters relative to zero output. The selected oxidant output parameters may be relative to (base) output parameters corresponding to a base output of oxidant at a default operational program or setting. In some examples, the operational program includes output parameters for a temporary boost mode corresponding to the selected oxidant output parameters. For example, the temporary boost mode output parameters may be relative to the current output parameters of the portable scent control device, such as a standard indoor mode or standard outdoor mode as adjusted according current local conditions.

The one or more selected oxidant output parameters are effective to cause the portable scent control device to emit oxidant at the selected oxidant output rate, such as at least 100 mg of oxidant per hour.

The one or more selected oxidant output parameters may include one or more of an amount electrical bias delivered to the portable oxidant generator (e.g., corona discharge electrode(s)), duration of electrical bias delivered to the portable oxidant generator, an amount or duration of electrical bias delivered to the at least one fan, durations of one or more pulses of electrical energy to the portable oxidant source, an amount of increase of electrical bias to the portable oxidant source over a base amount of bias responsive to initiation of the temporary boost mode, or a duration of the increased electrical bias to the portable oxidant source responsive to initiation of the temporary boost mode.

Automatically selecting an operational program responsive to receiving the one or more conditional inputs may include automatically selecting an operational program corresponding to a combination of the one or more conditional inputs that are input into the system, with a controller of the portable scent control device or a remote computing device operably coupled thereto. For example, automatically selecting an operational program responsive to receiving the one or more conditional inputs may include automatically correlating (e.g., with the controller or remote computing device) the one or more conditional inputs with a selected operational program that is composed to cause the portable scent control device to emit an oxidant at a selected rate that is effective to cause enough oxidant to be produced under current environmental conditions to at least partially dissociate scent molecules emanating from a user. The selected rate is sufficient to prevent an animal in an area where the portable scent control device is located from detecting the scent(s) of the user.

In examples, automatically selecting an operational program responsive to receiving the one or more conditional inputs includes automatically selecting an operational program that includes instructions for operating the portable scent control device at a higher oxidant output rate or a lower oxidant output rate than a base oxidant output rate (e.g. temporary boost mode) based on one or more conditional inputs. The one or more conditional inputs may include data communicating local conditions such as one or more of a wind speed, an elevation, a barometric pressure, a relative humidity, a temperature, a functional status of the portable scent control device, or indoor location of an area where the portable scent control device is located.

In examples, automatically selecting an operational program responsive to receiving the one or more conditional inputs may include continuously or intermittently selecting the operational program responsive to receiving the one or more conditional inputs. The continuous or intermittent selection may be carried out in intervals of at least 5 minutes, such as 5 minutes to 4 hours, 10 minutes to 2 hours, 15 minutes to 1 hour, 30 minutes to 1.5 hours, 1 hour to 3 hours, less than 4 hours, more than 1 hour, or more than 2 hours.

The method 700 includes the act 730 of automatically adjusting one or more output parameters of the portable scent control device to the one or more selected oxidant output parameters. Automatically adjusting one or more output parameters of the portable scent control device to the one or more selected oxidant output parameters may include adjusting the one or more output parameters from base, non-zero oxidant output parameters to the selected oxidant output parameters. Automatically adjusting one or more output parameters of the portable scent control device to the one or more selected oxidant output parameters may include adjusting the one or more output parameters from a base zero value for each of the oxidant output parameters.

In examples, automatically adjusting one or more operational parameters of the portable scent control device to the one or more selected oxidant output parameters is performed by the controller of the portable scent control device. The controller automatically adjusts the one or more operational parameters of the portable scent control device to the one or more selected oxidant output parameters according to the selected oxidant output parameters in the operational program. For example, a processor in the controller of the portable scent control device may access and execute an operational program stored in the memory of the controller to control the electrical bias applied to the portable oxidant source or one or more fans. In examples, automatically adjusting one or more operational parameters of the portable scent control device to the one or more selected oxidant output parameters may include providing instructions (e.g., electrical signals) to increase or decrease an amount of electrical bias applied to the portable oxidant generator or one or more fans (or a duration of the same) of the portable scent control device.

In examples, automatically adjusting one or more output parameters of the portable scent control device to the one or more selected oxidant output parameters may be carried out continuously, intermittently, or selectively (e.g., responsive only to a user command).

The method 700 includes the act 740 of outputting the oxidant from the portable scent control device at the selected oxidant output rate. As noted above, the portable scent control device may include any of the portable scent control devices disclosed herein. Outputting the oxidant from the portable scent control device at the selected oxidant output rate includes outputting one or more of ozone, diatomic oxygen, diatomic halogens, peroxides, radicals of any of the foregoing or components thereof, metastable oxygen, negatively charged metal oxides, encapsulated ozone, activated ozone, peracetic acid, chlorine dioxide, thixotropic gels, singlet oxygen, hypochlorite, or chlorite, from the portable scent control device. For example, outputting the oxidant from the portable scent control device at the selected oxidant output rate may include outputting ozone from a portable ozone generator at the selected oxidant (ozone) output rate. Even more specifically, outputting the oxidant from the portable scent control device at the selected oxidant output rate may include outputting ozone from a corona discharge ozone generator of the portable scent control device.

Outputting the oxidant from the portable scent control device at the selected oxidant output rate includes outputting the oxidant from the portable scent control device at any of the rates for any of the durations disclosed herein. Outputting the oxidant from the portable scent control device at the selected oxidant output rate may be carried out continuously or intermittently (e.g., pulses).

In examples, the method 700 includes positioning the portable scent control device adjacent to a user in an outdoor environment, in a container, or in a room. In examples, positioning the portable scent control device adjacent to the user may be carried out prior to or while outputting the oxidant from the portable scent control device at the selected oxidant output rate. In examples, positioning the portable scent control device adjacent to the user includes positioning the portable scent control device upwind from the user, on the user, on a piece of the user's equipment (e.g. pack), above the user, level with the user, downwind from the user, or in a user's blind.

The method 700 may include remotely activating a temporary boost mode operational program for temporarily increasing an amount of oxidant emitted from the portable scent control device to a selected amount for a selected duration. For example, the selected amount may include any of the boost mode amounts disclosed herein and the selected duration may include any of the durations disclosed herein. For example, the selected amount may include at least a 30% increase in oxidant emission over the selected oxidant output rate of the operational program and the selected duration includes at least 1 minute. In examples, remotely activating a boost mode operational program for temporarily increasing an amount of oxidant emitted from the portable scent control device to a selected amount for a selected duration includes activating the boost mode operational program with a remote control or remote input device operably coupled to the controller of the portable scent control device. In examples, the method 700 may include remotely activating a temporary boost mode for more than one scent control device, such as via a single remote control or remote input device. In such examples, a hunting guide may be able to activate the temporary boost mode of the scent control devices worn by a plurality of hunters and guides.

In examples, the method 700 may include determining one or more local conditions, such as via weather detection device such as a portable weather station, a wind meter, a temperature sensor, a barometer, altimeter, etc. The weather detection device may be operably coupled to the remote input device, the remote control, or the portable scent control device. Upon determining the one or more local conditions, the determined conditions may be manually input into the controller by the user or automatically input into the controller via the remote input device, remote control, or weather detection device.

Figure 8:
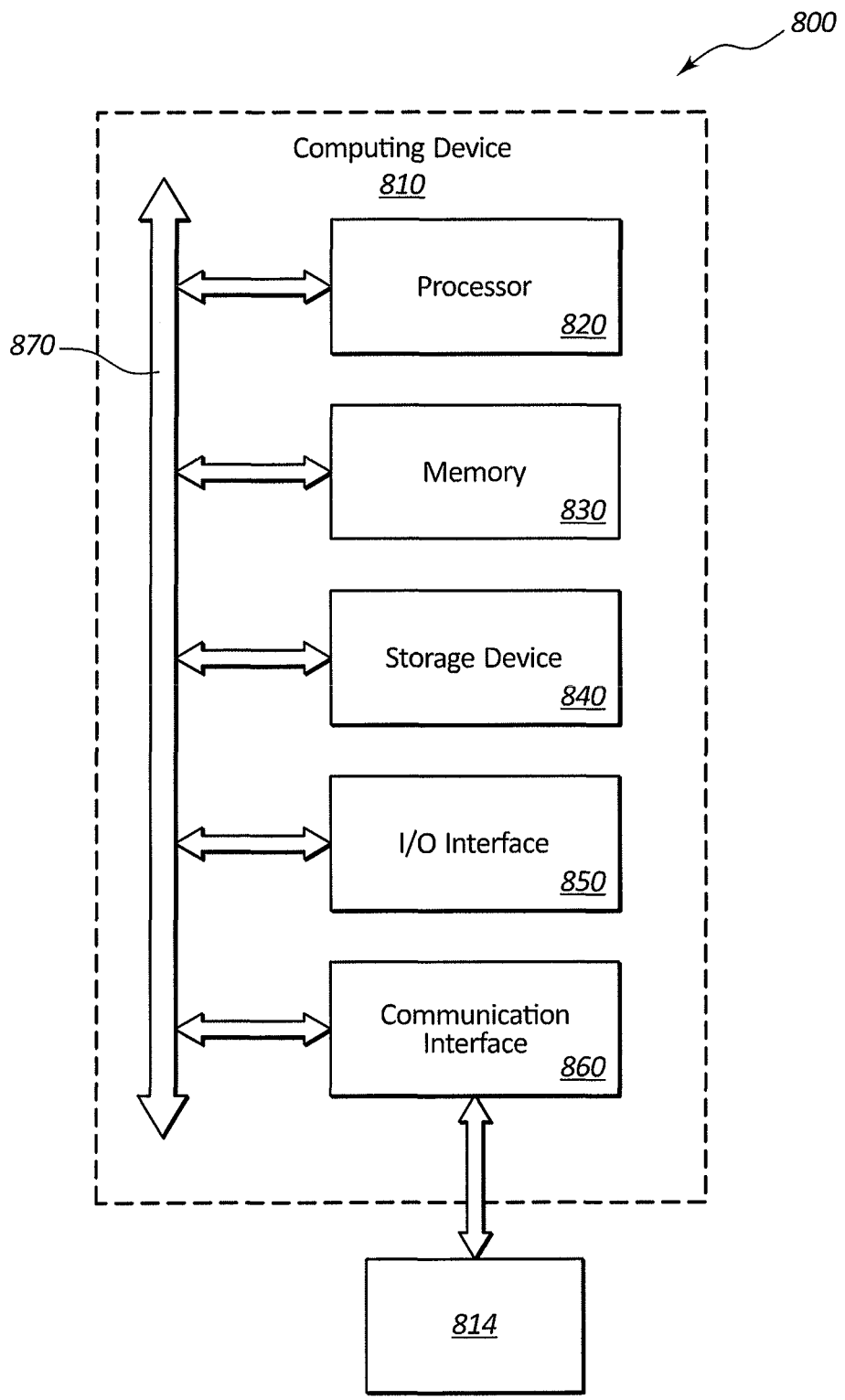
FIG. 8 is a block diagram of a controller for executing any of the example methods disclosed herein, according to at least some embodiments.

Any of the example controllers, computing devices, remote controls, remote input devices, or systems disclosed herein may be used to carry out any of the example methods disclosed herein. FIG. 8 is a block diagram of a controller 800 for executing any of the example methods disclosed herein, according to an embodiment. The controller 800 may be configured to implement any of the example methods disclosed herein, such as the method 700. The controller 800 includes at least one computing device 810. The at least one computing device 810 is an exemplary computing device that may be configured to perform one or more of the acts described above, such as the method 700. The at least one computing device 810 may include one or more servers, one or more computers (e.g., desk-top computer, lap-top computer), one or more mobile computing devices (e.g., smartphone, tablet, etc.), or one or more custom computing systems assembled to execute proprietary functions. The computing device 810 may comprise at least one processor 820, memory 830, a storage device 840, an input/output ("I/O") device/interface 850, and a communication interface 860. In examples, the computing device 810 may be sized to fit in another device, such as the housing of the portable scent control device.

While an example computing device 810 is shown in FIG. 8, the components illustrated in FIG. 8 are not intended to be limiting of the controller 800 or computing device 810. Additional or alternative components may be used in some examples. Further, in some examples, the controller 800 or the computing device 810 may include fewer components than those shown in FIG. 8. For example, the controller 800 may not include the one or more additional computing devices 812 (e.g., remote computing device). Rather, the one or more additional computing devices 812 may be separate and distinct from the computing device 810 of the controller 800. In some examples, the at least one computing device 810 may include connections to a plurality of computing devices, such as a server farm, computational network, or cluster of computing devices. Components of computing device 810 shown in FIG. 8 are described in additional detail below. In examples, the controller 800 or computing device 810 may be implemented as the controller 110 (FIG. 1).

In some examples, the processor(s) 820 includes hardware for executing operational programs or instructions (e.g., instructions for carrying out one or more portions of any of the methods disclosed herein), such as those making up a computer program. For example, to execute operational instructions, the processor(s) 820 may retrieve (or fetch) the operational instructions from an internal register, an internal cache, the memory 830, or a storage device 840 and decode and execute them. In particular examples, processor(s) 820 may include one or more internal caches for data such as oxidant output parameters or voltage amounts correlated to oxidant output parameters. As an example, the processor(s) 820 may include one or more instruction caches, one or more data caches, and one or more translation lookaside buffers (TLBs). Operational instructions in the instruction caches may be copies of instructions in memory 830 or storage device 840. In some examples, the processor 820 may be configured (e.g., include programming stored thereon or executed thereby) to carry out one or more portions of any of the example methods disclosed herein.

In some examples, the processor 820 is configured to perform any of the acts disclosed herein such as in method 700 or cause one or more portions of the computing device 810 or controller 800 to perform at least one of the acts disclosed herein. Such a configuration may include one or more operational programs (e.g., computer program products) that are executable by the at least one processor 820. For example, the processor 820 may be configured to automatically select an operational program responsive to receiving the one or more conditional inputs or automatically adjust one or more operational parameters of the portable scent control device to the one or more selected oxidant output parameters.

The at least one computing device 810 (e.g., a server) may include at least one memory storage medium (e.g., memory 830 and/or storage device 840). The computing device 810 may include memory 830, which is operably coupled to the processor(s) 820. The memory 830 may be used for storing data, metadata, and operational programs for execution by the processor(s) 820. The memory 830 may include one or more of volatile and non-volatile memories, such as Random Access Memory (RAM), Read Only Memory (ROM), a solid state disk (SSD), Flash, Phase Change Memory (PCM), or other types of data storage. The memory 830 may be internal or distributed memory.

The computing device 810 may include the storage device 840 having storage for storing data or instructions. The storage device 840 may be operably coupled to the at least one processor 820. In some examples, the storage device 840 may comprise a non-transitory memory storage medium, such as any of those described above. The storage device 840 (e.g., non-transitory storage medium) may include a hard disk drive (HDD), a floppy disk drive, flash memory, an optical disc, a magneto-optical disc, magnetic tape, or a Universal Serial Bus (USB) drive or a combination of two or more of these. Storage device 840 may include removable or non-removable (or fixed) media. Storage device 840 may be internal or external to the computing device 810. In some examples, storage device 840 may include non-volatile, solid-state memory. In some examples, storage device 840 may include read-only memory (ROM). Where appropriate, this ROM may be mask programmed ROM, programmable ROM (PROM), erasable PROM (EPROM), electrically erasable PROM (EEPROM), electrically alterable ROM (EAROM), or flash memory or a combination of two or more of these. In some examples, one or more portions of the memory 830 and/or storage device 840 (e.g., memory storage medium(s)) may store one or more databases thereon. At least some of the databases may be used to store one or more of local conditions, conditional inputs, correlations between conditional inputs and output parameters, or any other data as disclosed herein.

In some examples, one or more of operational programs (e.g., temporary boost mode operational programs), local conditions, conditional inputs, correlations between conditional inputs and output parameters, or any other data, may be stored in a memory storage medium such as one or more of the at least one processor 820 (e.g., internal cache of the processor), memory 830, or the storage device 840. In some examples, the at least one processor 820 may be configured to access (e.g., via bus 870) the memory storage medium(s) such as one or more of the memory 830 or the storage device 840. For example, the at least one processor 820 may receive and store the data (e.g., look-up tables) as a plurality of data points in the memory storage medium(s). The at least one processor 820 may execute programming stored therein adapted access the data in the memory storage medium(s) to perform any of the acts disclosed herein.

The computing device 810 also includes one or more I/O devices/interfaces 850, which are provided to allow a user to provide input to, receive output from, and otherwise transfer data to and from the computing device 810. These I/O devices/interfaces 850 may include a mouse, keypad or a keyboard, a touch screen, camera, optical scanner, network interface, web-based access, modem, a port, other known I/O devices, any of the one or more selectors disclosed herein, or a combination of such I/O devices/interfaces 850. The one or more selectors may be manipulated by a stylus or a finger. The touch screen may be activated with a stylus or a finger.

The I/O devices/interfaces 850 may include one or more devices for presenting output to a user, including, but not limited to, a graphics engine, a display (e.g., a display screen or monitor), one or more output drivers (e.g., display drivers), one or more audio speakers, and one or more audio drivers. In certain examples, I/O devices/interfaces 850 are configured to provide graphical data to a display for presentation to a user. The graphical data may be representative of one or more graphical user interfaces and/or any other graphical content as may serve a particular implementation.

The computing device 810 may further include a communication interface 860 (e.g., data connection 160 of FIG. 1). The communication interface 860 may include hardware, software, or both. The communication interface 860 may provide one or more interfaces for communication (such as, for example, packet-based communication) between the computing device 810 and one or more additional computing devices 812 or one or more networks. For example, communication interface 860 may include a network interface controller (NIC) or network adapter for communicating with an Ethernet or other wire-based network or a wireless NIC (WNIC) or wireless adapter for communicating with a wireless network, such as a WI-FI.

Any suitable network and any suitable communication interface 860 may be used. For example, computing device 810 may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, one or more portions of controller 800 or computing device 810 may communicate with a wireless PAN (WPAN) (such as, for example, a BLUETOOTH WPAN), a WI-FI network, a WI-MAX network, a cellular telephone network (such as, for example, a GSM network), or other suitable wireless network or a combination thereof. Computing device 810 may include any suitable communication interface 860 for any of these networks, where appropriate.

The computing device 810 may include the bus 870. The bus 870 may include hardware, software, or both that couples components of computing device 810 to each other. For example, bus 870 may include an Accelerated Graphics Port (AGP) or other graphics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination thereof.

It should be appreciated that any of the examples of acts described herein, such as in the method 700 may be performed by and/or at the controller 800 or computing device 810 thereof. As noted the computing device 810 may be sized, shaped, and otherwise configured to fit one or within the portable scent control devices or systems disclosed herein. The operational programs may be stored and/or executed by the controller 800 or the computing device 810 therein.

Figure 9:
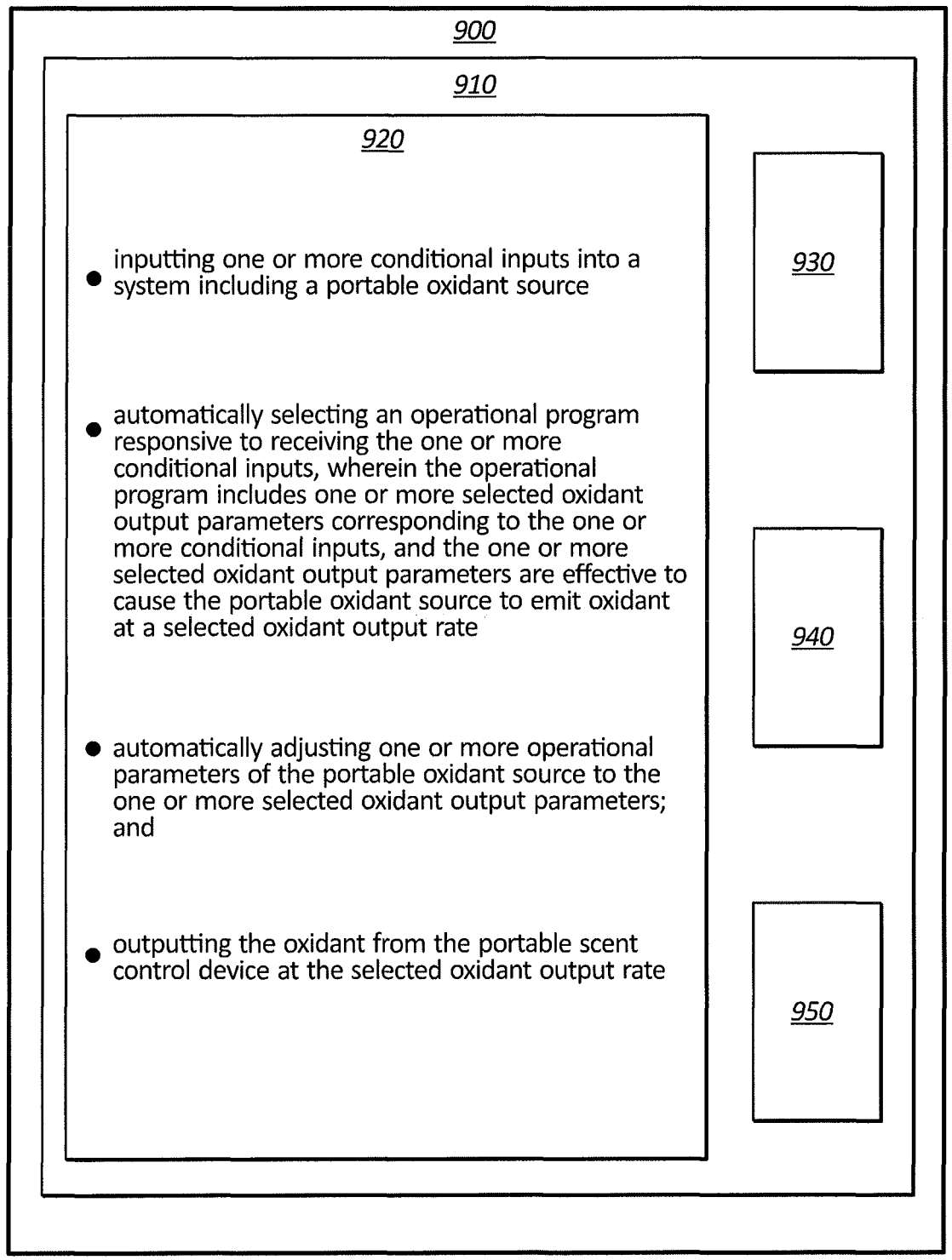
FIG. 9 is a block diagram of an example computer program product, according to at least some embodiments.

FIG. 9 is a block diagram of an example computer program product 900, according to an embodiment. The computer program product 900 is arranged to store operational instructions for selectively emitting scent control material responsive to local conditions of a scent control device as disclosed herein with respect to the scent control methods, systems, and devices. The non-transitory signal bearing medium 910 may include a computer-readable medium 930 (e.g., read-only memory, RAM, hard drive such as a magnetic disc drive or solid state disc, flash memory stick, internal cache of a processor, or optical disc), a computer recordable medium 940 (e.g., RAM, hard drive, memory stick, optical disc, etc.), a computer communications medium 950 (e.g., internal cache of a BUS, etc.), or combinations thereof. The non-transitory signal bearing medium 910 stores programming instructions 920 (e.g., computer code describing one or more operational instructions or programs) that may configure the processing unit of an associated controller or computer storing the same to perform all or some of the methods or acts described herein. The operational instructions may include, for example, one or more machine readable and executable instructions for "inputting one or more conditional inputs into a system including a portable scent control device." These operational instructions may include, for example, one or more machine readable and executable instructions for "automatically selecting an operational program responsive to receiving the one or more conditional inputs, wherein the operational program includes one or more selected oxidant output parameters corresponding to the one or more conditional inputs, and the one or more selected oxidant output parameters are effective to cause the portable scent control device to emit oxidant at a selected oxidant output rate." The operational instructions may include, for example, one or more machine readable and executable instructions for "automatically adjusting one or more output parameters of the portable scent control device to the one or more selected oxidant output parameters." The operational instructions may include, for example, one or more machine readable and executable instructions for "outputting the oxidant from the portable scent control device at the selected oxidant output rate." In examples, the operational instructions may include any portions of the method 700 disclosed herein, in any combination.

The computer program product 900 is readable and executable by the one or more of the controllers, remoted computing devices, or remote input devices disclosed herein. For example, the controller of the portable scent control devices may have the computer program product 900 stored therein. The controller may access and execute one more operational programs of the computer program product 900, such as responsive to receiving conditional inputs or a code identifying a selected operational program.

In some examples, the endpoint values disclosed herein may be approximate values, which may vary by 10% or less from the precise endpoint value given. In such examples, the term "about" or "substantially" may indicate the approximate values.

Aspects of any of the examples disclosed herein may be used with aspects of any other examples, disclosed herein without limitation.

While various aspects and embodiments have been disclosed herein, other aspects and embodiments are contemplated. The various aspects and embodiments disclosed herein are for purposes of illustration and are not intended to be limiting. Additionally, the words "including," "having," and variants thereof (e.g., "includes" and "has") as used herein, including the claims, shall be open ended and have the same meaning as the word "comprising" and variants thereof (e.g., "comprise" and "comprises").

What is claimed is:

1. A scent control device, comprising:
   a portable oxidant source;
   a controller operably coupled to the portable oxidant source, the controller including one or more operational programs stored therein to control output of an oxidant from the portable oxidant source, each of the one or more operational programs including oxidant output parameters for outputting an amount of oxidant corresponding to a combination of one or more conditional inputs indicating local conditions of the scent control device, wherein the one or more operational programs include a temporary boost mode operational program for temporarily increasing an amount of oxidant emitted from the portable oxidant source to a selected amount for a selected duration which includes directions to increase an output of the portable oxidant source by at least 30% for a duration of at least 1 minute over a current emission output of the portable oxidant source prescribed by the one or more conditional inputs, wherein the one or more operational programs further include instructions for increasing oxidant output parameters at relatively higher elevations or lower barometric pressures over base oxidant output parameters; and one or more selectors operably coupled to the controller for inputting the one or more conditional inputs into the controller, the one or more selectors including at least one of a plurality of direct inputs coupled to the portable oxidant source or a data connection for a network device coupled to the portable oxidant source, the network device having access to location data for an area in which the portable oxidant source is located.

2. The scent control device of claim 1, wherein the portable oxidant source includes a corona discharge ozone generator.

3. The scent control device of claim 1, wherein the portable oxidant source includes a source of one or more of ozone, diatomic oxygen, diatomic halogens, peroxides, radicals of any of the foregoing or components thereof, metastable oxygen, negatively charged metal oxides, encapsulated ozone, activated ozone, peracetic acid, chlorine dioxide, thixotropic gels, singlet oxygen, hypochlorite, or chlorite.

4. The scent control device of claim 1, wherein the local conditions include one or more of a wind speed, an elevation, a barometric pressure, a relative humidity, a temperature, or indoor location of an area where the portable oxidant source is located.

5. The scent control device of claim 4, wherein the local conditions include a functional status of the portable oxidant source.

6. The scent control device of claim 1, wherein each of the plurality of direct inputs corresponds to one of the one or more conditional inputs including a wind speed conditional input, an elevation conditional input, a barometric pressure conditional input, a relative humidity conditional input, a temperature conditional input, or an indoor conditional input.

7. The scent control device of claim 6, wherein the output parameters of the one or more operational programs are composed to direct a selected amount of oxidant output per unit time based upon a value of a combination of the conditional inputs.

8. The scent control device of claim 6, wherein the output parameters of the one or more operational programs are composed to direct a selected amount of oxidant output per unit time for a selected duration based upon a value of a combination of the conditional inputs.

9. The scent control device of claim 1, wherein the location data includes global positioning coordinates corresponding to the area in which the portable oxidant source is disposed and the one or more conditional inputs including a wind speed conditional input, an elevation conditional inputs, a barometric pressure conditional input, a relative humidity conditional input, a temperature conditional input, or an indoor conditional input, corresponding to the global positioning coordinates.

10. The scent control device of claim 9, wherein the output parameters of the one or more operational programs are composed to direct a selected amount of oxidant output per unit time based upon a value of a combination of the conditional inputs.

11. The scent control device of claim 9, wherein the data connection includes one or more of a wired connection, a Bluetooth port, an infrared port, a radio frequency port, or a Wi-Fi port.

12. The scent control device of claim 1, further comprising a remote control operably coupled to the controller, wherein the remote control is configured to initiate or terminate generation of oxidant, adjust an amount of oxidant output from the portable oxidant source, input the one or more conditional inputs, or initiate the temporary boost mode.

13. The scent control device of claim 1, further comprising a fan operably coupled to the controller and positioned to propel oxidant away from the portable oxidant source.

14. The scent control device of claim 13, further comprising a power supply operably coupled to the portable oxidant source, the controller, and the fan.

15. The scent control device of claim 14, further comprising a housing containing the power supply, the portable oxidant source, the controller, and the fan.

16. A scent control system, comprising:
a portable scent control device, including:
an oxidant generator configured to generate and output ozone; and
a controller operably coupled to the oxidant generator, the controller including one or more operational programs stored therein to control output of an oxidant from the portable scent control device, the oxidant including ozone, each of the one or more operational programs including oxidant output parameters for generating and outputting an amount of oxidant corresponding to a combination of one or more conditional inputs indicating local conditions of the scent control device, the local conditions including one or more of an elevation or a barometric pressure of an area where the portable oxidant source is located, and wherein the operational programs include instructions for one or more of increasing oxidant output parameters at relatively higher elevations or increasing oxidant output parameters at relatively lower barometric pressures over base oxidant output parameters;
one or more selectors operably coupled to the controller for inputting the one or more conditional inputs corresponding to local conditions of the portable scent control device into the controller, the one or more selectors including a data connection for at least one remote device coupled to the portable oxidant source; and
a remote computing system operably coupled to the one or more selectors, the remote computing system including at least one database of conditional inputs and corresponding oxidant output operational programs, the remote computing system having access to location data for an area in which the portable oxidant source is located.

17. The scent control system of claim 16, wherein the one or more selectors are operably coupled to at least one remote input device operably coupled to the remote computing system, wherein the remote input device is configured to initiate or terminate generation of oxidant, adjust an amount of oxidant output from the portable scent control device, input the one or more conditional inputs, or initiate a temporary boost mode.

18. The scent control system of claim 17, wherein the at least one remote input device includes one or more of a remote control, a cellular phone, a satellite phone, or a global positioning system receiver.

19. The scent control system of claim 17, wherein the remote input device includes a cellular phone with global positioning system capabilities operably coupled to the one or more selectors and the cellular phone is operably coupled to the remote computing system via one or more of Wi-Fi, cellular network, Bluetooth, or satellite network connection.

20. The scent control system of claim 19, wherein:
the cellular phone is configured to receive global positioning coordinates of a location of the portable scent control device and communicate the global positioning coordinates to the remote computing system;
the remote computing system is configured to:
receive the global positioning coordinates from the cellular phone;
access a database of current conditional inputs corresponding to the location of the global positioning coordinates; and
communicate the current conditional inputs to the cellular phone; and
the cellular phone is configured to communicate the current conditional inputs to the one or more selectors effective to initiate a selected operational program stored in the controller corresponding to the current conditional inputs to control production of the oxidant at a selected rate.

21. The scent control system of claim 19, wherein:
the cellular phone is configured to receive global positioning coordinates of a location of the portable scent control device and communicate the global positioning coordinates to the remote computing system;
the remote computing system is configured to:
receive the global positioning coordinates from the cellular phone;
access a database of current conditional inputs for the location of the global positioning coordinates;
correlate the one or more of the current conditional inputs with a selected operational program composed to cause the portable scent control device to produce oxidant at a selected rate; and
communicate the selected operational program to the cellular phone; and
the cellular phone is configured to communicate the selected operational program with the controller effective to initiate production of the oxidant at the selected rate.

22. The scent control system of claim 21, wherein the selected rate is effective to cause enough of the oxidant to be emitted under current environmental conditions to at least partially dissociate scent molecules emanating from a user sufficient to prevent an animal in the location of the portable scent control device from detecting a scent of the user.

23. The scent control system of claim 16, further comprising a remote control operably coupled to the controller, wherein the remote control is configured to initiate or terminate generation of oxidant, adjust an amount of oxidant output from the portable scent control device, input one or more conditional inputs, or place the portable scent control device in a temporary boost mode.

24. The scent control system of claim 16, wherein a boost mode operational program for temporarily increasing an amount of oxidant emitted from the portable scent control device to a selected amount for a selected duration includes directions to increase an output of the portable scent control device by at least 30% for a duration of at least 1 minute.

25. The scent control system of claim 16, wherein the local conditions include one or more of a wind speed or a temperature of an area where the portable scent control device is located.

26. The scent control system of claim 16, wherein the local conditions includes an efficiency of the oxidant generator.

* * * * *